United States Patent
Kim et al.

(10) Patent No.: US 11,478,195 B2
(45) Date of Patent: Oct. 25, 2022

(54) MULTI-SENSOR PLATFORM FOR DIAGNOSING CATHETER STATUS

(71) Applicant: UNIVERSITY OF SOUTHERN CALIFORNIA, Los Angeles, CA (US)

(72) Inventors: Brian J. Kim, Los Angeles, CA (US); Lawrence Yu, Los Angeles, CA (US); Ellis Meng, La Canada Flintridge, CA (US); Alexander Baldwin, Tyler, TX (US)

(73) Assignee: University of Southern California, Los Angeles, CA (US)

( * ) Notice: Subject to any disclaimer, the term of this patent is extended or adjusted under 35 U.S.C. 154(b) by 608 days.

(21) Appl. No.: 15/543,506

(22) PCT Filed: Jan. 13, 2016

(86) PCT No.: PCT/US2016/013169
§ 371 (c)(1),
(2) Date: Jul. 13, 2017

(87) PCT Pub. No.: WO2016/115208
PCT Pub. Date: Jul. 21, 2016

(65) Prior Publication Data
US 2018/0000421 A1 Jan. 4, 2018

Related U.S. Application Data

(60) Provisional application No. 62/103,369, filed on Jan. 14, 2015.

(51) Int. Cl.
*A61B 5/00* (2006.01)
*A61B 5/03* (2006.01)
(Continued)

(52) U.S. Cl.
CPC .......... *A61B 5/6852* (2013.01); *A61B 5/0004* (2013.01); *A61B 5/031* (2013.01);
(Continued)

(58) Field of Classification Search
CPC ........ A61B 5/14507; A61B 2560/0219; A61B 5/0004; A61B 5/01; A61B 5/031;
(Continued)

(56) References Cited

U.S. PATENT DOCUMENTS

| 4,246,908 A | 1/1981 | Igarashi et al. |
| 4,593,703 A | 6/1986 | Cosman |

(Continued)

FOREIGN PATENT DOCUMENTS

WO      2010098868 A1      9/2010

OTHER PUBLICATIONS

International Search Report and Written Opinion from PCT Application No. PCT/US2016/013169, dated May 19, 2016, 14 pages.
(Continued)

*Primary Examiner* — Brandy S Lee
(74) *Attorney, Agent, or Firm* — McDermott Will & Emery LLP

(57) ABSTRACT

A multi-sensor system may include a catheter that has lumen, is flexible, is made of a polymer, and has a circular cross section that has an outer diameter of no more than 0.5 cm; and one or more sensors that sense multiple characteristics of material flowing within the lumen, including at least two of the following: flow rate, pressure, and composition of the material. A multi-sensor system may include a catheter that has lumen, is flexible, is made of a polymer, and has a circular cross section that has an outer diameter of no more than 0.5 cm; and one or more sensors that sense multiple
(Continued)

characteristics of material flowing within the lumen, including at least two of the following: flow rate, pressure, and composition of the material.

10 Claims, 21 Drawing Sheets

(51) Int. Cl.
*A61B 5/145* (2006.01)
*A61B 5/0538* (2021.01)
*A61L 29/04* (2006.01)
*A61L 29/14* (2006.01)
*A61B 5/01* (2006.01)
*G01F 1/64* (2006.01)
*G01N 27/27* (2006.01)

(52) U.S. Cl.
CPC ............ *A61B 5/036* (2013.01); *A61B 5/0538* (2013.01); *A61B 5/14507* (2013.01); *A61B 5/686* (2013.01); *A61L 29/041* (2013.01); *A61L 29/14* (2013.01); *A61B 5/01* (2013.01); *A61B 2560/0219* (2013.01); *G01F 1/64* (2013.01); *G01N 27/27* (2013.01)

(58) Field of Classification Search
CPC ..... A61B 5/036; A61B 5/0538; A61B 5/6852; A61B 5/686; G01F 1/64
See application file for complete search history.

(56) References Cited

U.S. PATENT DOCUMENTS

| | | | |
|---|---|---|---|
| 4,676,255 A | 6/1987 | Cosman | |
| 5,026,348 A | 6/1991 | Venegas | |
| 5,935,084 A | 8/1999 | Southworth | |
| 6,248,080 B1 | 6/2001 | Miesel et al. | |
| 6,533,733 B1 | 3/2003 | Ericson et al. | |
| 6,537,232 B1 | 3/2003 | Kucharczyk et al. | |
| 8,088,091 B2 | 1/2012 | Thomas et al. | |
| 8,192,366 B2 | 6/2012 | Mauge et al. | |
| 8,457,733 B2 | 6/2013 | Linninger | |
| 8,480,612 B2 | 7/2013 | Kassem | |
| 8,734,718 B2 | 5/2014 | Dacey et al. | |
| 2004/0068201 A1* | 4/2004 | Saul | A61M 27/006 600/561 |
| 2006/0020239 A1 | 1/2006 | Geiger et al. | |
| 2008/0302675 A1* | 12/2008 | Hsiai | A61B 5/01 205/777.5 |
| 2009/0204019 A1* | 8/2009 | Ginggen | A61B 5/031 600/561 |
| 2010/0160755 A1* | 6/2010 | Oviatt | C12Q 1/54 600/345 |
| 2012/0265028 A1 | 10/2012 | Hughes et al. | |
| 2013/0102951 A1 | 4/2013 | Swoboda et al. | |
| 2013/0109998 A1 | 5/2013 | Swoboda et al. | |
| 2013/0202721 A1* | 8/2013 | Silver | A61B 5/0031 424/718 |
| 2013/0237780 A1* | 9/2013 | Beasley | A61B 18/1492 600/309 |
| 2013/0245403 A1 | 9/2013 | Geifer et al. | |
| 2013/0247644 A1 | 9/2013 | Swoboda et al. | |
| 2015/0297093 A1 | 10/2015 | Goldie et al. | |
| 2015/0305629 A1 | 10/2015 | Fritz et al. | |

OTHER PUBLICATIONS

Cinalli, G., et al., "The role of endoscopic third ventriculostomy in the management of shunt malfunction," Neurosurgery, vol. 43, pp. 1323-1327, 1998.
Hakim, C., et al., "Normal-pressure hydrocephalus," Neurosurgery clinics of North America, vol. 12, pp. 761-73, ix, 2001.
Rocque, B. G., et al., "Venticular shunt tap as a predictor of proximal shunt malfunction in children: a prospective study," 2008.
Sood, S., et al., "Useful components of the shunt tap test for evaluation of shunt malfunction," Child's Nervous System, vol. 9, pp. 157-161, 1993.
Stephens, L.C., et al., "Are clinical signs accurate indicators of the cause of central venous catheter occlusion?," Journal of Parental and Enteral Nutrition, vol. 19, pp. 75-79, 1995.
Yu, L., et al., "A Microbubble Pressure Transducer with Bubble Nucleation Core," in Micro Electro Mechanical Systems (MEMS), 2014 IEEE 27th International Conference on, 2014, pp. 104-107.
Zorc, J.J., et al., "Radiographic Evaluation for Suspected Cerebrospinal Fluid Shunt Obstruction," Pediatric Emergency Care, vol. 18, pp. 337-340, 2002.

* cited by examiner

MULTI-SENSOR PLATFORM FOR DIAGNOSING CATHETER STATUS

CROSS-REFERENCE TO RELATED APPLICATION

This application is based upon and claims priority to U.S. provisional patent application No. 62/103,369, entitled "Multi-Sensor Platform for Diagnosing Catheter Status," filed Jan. 14, 2015. The entire content of this application is incorporated herein by reference.

STATEMENT REGARDING FEDERALLY SPONSORED RESEARCH

This invention was made with government support under Grant No. EFRI-1332394, awarded by the National Science Foundation (NSF). The government has certain rights in the invention."

BACKGROUND

Technical Field

This disclosure relates to catheter flow sensors.

Description of Related Art

Catheters may be implanted into a brain ventricle for draining excess cerebrospinal fluid in the treatment of hydrocephalus. Hydrocephalus is a chronic, incurable condition of the excess accretion of cerebrospinal fluid (CSF) generating high intracranial pressures within the ventricles of the brain. A properly placed ventricular shunt/valve can drain the excess CSF and effectively treat the condition, however, the failure rate of these shunts is high. The most prevalent failure mode is obstruction of the holes responsible for drainage. A large unmet need is early diagnosis of this and other forms of shunt malfunction, which is currently difficult, unreliable, and costly.

Shunt failure can be progressive and associated with vague symptoms, such as nausea, headaches, and irritability. Imaging techniques (e.g. MRI [G. Cinalli, C. Salazar, C. Mallucci, J. Z. Yada, M. Zerah, and C. Sainte-Rose, "The role of endoscopic third ventriculostomy in the management of shunt malfunction," *Neurosurgery*, vol. 43, pp. 1323-1327, 1998.] or CT scans [J. J. Zorc, S. D. Krugman, J. Ogborn, and J. Benson, "Radiographic evaluation for suspected cerebrospinal fluid shunt obstruction," *Pediatric Emergency Care*, vol. 18, pp. 337-340, 2002.]) or shunt taps (aspirating the shunt) [B. G. Rocque, S. Lapsiwala, and B. J. Iskandar, "Ventricular shunt tap as a predictor of proximal shunt malfunction in children: a prospective study," 2008.; S. Sood, S. Kim, S. Ham, A. Canady, and N. Greninger, "Useful components of the shunt tap test for evaluation of shunt malfunction," *Child's Nervous System*, vol. 9, pp. 157-161, 1993.] have been used to diagnose obstructed shunts, but a definitive diagnosis was sometimes only possible by surgically removing the shunt. Such a surgical procedure can be undesirable, costly, and untimely.

In vivo pressure sensor technology has enabled measurements within the body [E. R. Cosman, "Telemetric differential pressure sensor with the improvement of a conductive shorted loop tuning element and a resonant circuit," U.S. Pat. No. 4,593,703 A, 1986.; E. R. Cosman, "Telemetric in-vivo calibration method and apparatus using a negative pressure applicator," U.S. Pat. No. 4,676,255 A, 1987.; M. N. Ericson, T. E. Mcnight, S. F. Smith, and J. O. Hylton, "Implantable device for in-vivo intracranial and cerebrospinal fluid pressure monitoring," U.S. Pat. No. 6,533,733 B1, 2003.; A. Ginggen and Y. Tandy, "Combined pressure and flow sensor integrated in a shunt system," US 20090204019 A1, 2009.; K. Hughes and A. Strachan, "Sensor, circuitry, and method for wireless intracranial pressure monitoring," US 20120265028 A1, 2012.; H. Inagaki, M. Mizuno, and I. Igarashi, "Intracranial pressure transducer," U.S. Pat. No. 4,246,908 A, 1981.; S. Kassem, "Wireless shunts with storage," U.S. Pat. No. 8,480,612 B2, 2013.; K. A. Miesel and L. Stylos, "Intracranial monitoring and therapy delivery control device, system and method," U.S. Pat. No. 6,248,080 B1, 2001.; C. B. Southworth, "Inflatable pressure indicator," U.S. Pat. No. 5,935,084 A, 1999.; M. Swoboda, M. G. Hochman, M. Mattiucci, and F. Fritz, "Implantable pressure sensor," US 20130247644 A1, 2013.; G. A. Thomas, R. C. Farrow, and S. Liu, "No clog shunt using a compact fluid drag path," U.S. Pat. No. 8,088,091 B2, 2012.; J. G. Venegas, "Apparatus and method for the detection of IV catheter obstruction and extravasation," U.S. Pat. No. 5,026,348 A, 1991.; C. Mauge, A. J. Dextradeur, D. J. McCusker, S. Meyer, V. Boedecker, R. G. Kraus, et al., "Method for measuring ventricular pressure using a pressure sensing valve," ed: US 8192366 B2, 2012.; J. Kucharczyk and C. L. Truwit, "Intracranial pressure monitoring device and method for use in MR-guided drug delivery," US 6537232 B1, 2003.; K. A. Miesel and L. Stylos, "Intracranial monitoring and therapy delivery control device, system and method," US 6248080 B1, 2001.; C. B. Southworth, "Inflatable pressure indicator," US 5935084 A, 1999.; E. R. Cosman, "Telemetric in-vivo calibration method and apparatus using a negative pressure applicator," US 4676255 A, 1987.; H. Inagaki, M. Mizuno, and I. Igarashi, "Intracranial pressure transducer," US 4246908 A, 1981.]. Various devices have been developed to measure flow within catheters [M. Geiger and L. Speckman, "Cerebral spinal fluid flow sensing device," US 20060020239 A1, 2006.; S. Kassem, "Wireless flow sensor," US 20130245403 A1, 2013.; M. Swoboda, M. G. Hochman, M. E. Mattiucci, and F. J. Fritz, "CSF shunt flow enhancer, method for generating CSF flow in shunts and assessment of partial and complete occlusion of CSF shunt systems," US 20130102951 A1, 2013.; M. Swoboda, M. G. Hochman, M. E. Mattiucci, and F. J. Fritz, "Real time CSF flow measurement system & method," US 20130109998 A1, 2013.]. They [T. Saul, "Systems and methods for flow detection and measurement in CSF shunts," US 2004068201 A1, 2003.; F. J. Fritz, M. Swoboda, M. E. Mattiucci, and M. G. Hochman, "CSF SHUNT FLOW EVALUATION APPARATUS AND METHOD USING A CONFORMABLE EXPANDED DYNAMIC RANGE THERMOSENSOR," US 20150305629 A1, 2015.; J. H. Goldie, T. Q. Truong, M. Duong, and T. Russell, "Flow rate sensor system and method for non-invasively measuring the flow rate of a bodily fluid," US 20150297093 A1, 2015.; M. Swoboda, M. G. Hochman, M. E. Mattiucci, and F. J. Fritz, "Real time CSF flow measurement system and method," US 20130109998 A1,2014.] use various flow sensors that track the passage of a localized region of heat. Mechanical sensing elements that deform under flow have also been implemented as implantable radio frequency (RF) tags [S. Kassem, "Wireless flow sensor," US 20130245403 A1, 2013.].

In addition to electrical sensing methods [A. Linninger, "Monitoring and controlling hydrocephalus," US 20100130884 A1, 2013.], optical means have been proposed to track the flow rate via a laser Doppler [M. Geiger and L. Speckman, "Cerebral spinal fluid flow sensing device," US 20060020239 A1, 2004.] or movement of particles in the cerebrospinal fluid (CSF) as they traverse fluidic channels [Searette LLC, R. G. Dacey, R. A. Hyde, M. Y. Ishikawa, J. T. Kare, E. C. Leuthardt, N. P. Myhrvold, et al., "Systems, devices, and methods including infection-fighting and monitoring shunts," WO 2010098868 A1, 2010.]. The use of electrochemical impedance measurements to determine volume of the CSF within the ventricles can provide additional insight on CSF dynamics that could be useful for assessing shunts [A. Linninger, "Monitoring and controlling hydrocephalus," U.S. Pat. No. 8,457,733 B2, 2010.]; however, it may not be compatible for use as an implanted sensor for long term monitoring.

These methods may require direct contact of the transducer with a corrosive, high salinity in vivo environment. This may require the use of bulky hermetic packaging to protect the electronic portion of the sensing element. The aforementioned difficulties might be avoided through the use of noninvasive interrogation techniques, but may be at the cost of greatly reduced resolution and sensitivity, which may then impact diagnosis and treatment.

Catheter failures can be systemic problems that cannot be measured by a single parameter. In normal pressure hydrocephalus, a condition with symptoms similar to conventional hydrocephalus, fluid blockage can occurs, but intracranial pressure buildup may not be observable [C. Hakim, R. Hakim, and S. Hakim, "Normal-pressure hydrocephalus," *Neurosurgery clinics of North America*, vol. 12, pp. 761-73, ix, 2001.]. Such a condition may require information from multiple sensors to be diagnosed properly. For central venous catheters, occlusion can occur for reasons such as a thrombotic clot or mechanical malfunction [L. C. Stephens, W. D. Haire, and G. D. Kotulak, "Are clinical signs accurate indicators of the cause of central venous catheter occlusion?," *Journal of Parenteral and Enteral Nutrition*, vol. 19, pp. 75-79, 1995.]

The use of single sensor can limit the quantitative information that can be obtained and any single measure may not be sufficient to diagnose shunt malfunction. There have been efforts to develop systems that incorporate multiple sensing elements. Pressure and orientation (via accelerometer/gyro) sensors were combined to measure ICP with respect to postural changes [K. Hughes and A. Strachan, "Sensor, circuitry, and method for wireless intracranial pressure monitoring," US 20120265028 A1,2012.]. Flow and pressure information were collected and processed with a microcontroller, and subsequently wirelessly transmitted [M. N. Ericson, T. E. McKnight, S. F. Smith, and J. O. Hylton, "Implantable device for in-vivo intracranial and cerebrospinal fluid pressure monitoring," US 6533733 B1, 2003.; A. Ginggen and Y. Tardy, "Combined Pressure and Flow Sensor Integrated in a Shunt System," US 20090204019 A1,2008.]. Finally, a variety of information (e.g. pH, blood oxygen, pressure, ICP, respiratory rate) was incorporated into a system for infection fighting and monitoring of shunts [R. G. Dacey, R. A. Hyde, M. Y. Ishikawa, J. T. Kare, E. C. Leuthardt, N. P. Myhrvold, et al., "Systems, devices, and methods including catheters having an actively controllable therapeutic agent delivery component," US 8723718 A1, 2014.].

Although many strategies to measure pressure, flow rate, and related parameters have been explored, the current state of the art typically uses a single sensor type or adaptation of sensor developed for dry applications. A single sensor type may not provide sufficient data on the multiple processes of interest at play in biological systems that impact their hydrodynamics. Sensor types developed for non-biological purposes may suffer from performance degradation when the required hermetic or protective coatings are applied.

SUMMARY

A multi-sensor system may include a catheter that has lumen, is flexible, is made of a polymer, and has a circular cross section that has an outer diameter of no more than 0.5 cm; and one or more sensors that sense multiple characteristics of material flowing within the lumen, including at least two of the following: flow rate, pressure, and composition of the material.

At least a portion of the one or more sensors may be within the lumen.

A portion of the one or more sensors may be located on a flexible substrate that is separate from the catheter.

The flexible substrate may be Parylene C.

When the portion of the one or more sensors are within the lumen, they may not materially block the material from flowing within the lumen and/or may not protrude within the lumen by more than 50 microns.

The catheter may have an interior wall that defines the lumen and a portion of the one or more sensors may be located on a portion of the interior wall.

The multi-sensor system may include including a wireless communication system that wirelessly communicates information from the one or more sensors.

The multi-sensor system may include an inductor that wirelessly receives power that powers the one or more sensors.

The multi-sensor system may include a data processing system that performs computations on data generated by the one or more sensors.

The one or more sensors may include a sensor that uses electrochemical transduction to determine a characteristic of the material flowing in the lumen.

A flow sensor system may include a sensor that senses material flow; a fluid disrupter that transiently perturbs the electrochemical impedance of material flowing by the sensor; and one or more electrodes that measure the electrochemical impedance of material flowing by the sensor.

The sensor may be within or on a flexible substrate.

The flexible substrate may be Parylene C.

The electrodes may be platinum.

The fluid disrupter may include a heater that heats the flowing material to perturb the flowing material. The heater may include a resistive heating element. The resistive heating element may include a serpentine platinum wire.

The fluid disrupter may include a gas bubble generator. The gas bubble generator may generate one or more gas bubbles using electrolysis driven by at least two electrodes.

The one or more electrodes may measure the electrochemical impedance after the electrochemical impedance has been perturbed.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

FIG. 4A illustrates an example of two electrodes placed on the interior and exterior of the catheter for impedance measurement. FIG. 4B illustrates an example of obstruction of a port by tissue or cellular debris. FIG. 4C illustrates an example of how this obstruction interferes with the conduction path between the electrodes, causing the impedance to increase.

FIG. 9A illustrates an example of a cap module. A 3 way valve may be used for fluidic interconnect between the device and the catheter. The catheter was placed within a beaker of artificial cerebrospinal fluid and was filled using a syringe or peristaltic pump. The impedance was measured between the sensor and a platinum wire also present in the beaker. FIG. 9B illustrates an example of an inline module which may remove the need for a 3-way valve and may allow for a direct connection between the catheter and a syringe or peristaltic pump. The impedance was also measured between the sensor and a platinum wire present in the beaker.

DETAILED DESCRIPTION OF ILLUSTRATIVE EMBODIMENTS

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

Overview

Multi-sensor systems for use in the diagnosis of the state of implanted drainage catheters are now described. To provide a quantitative, continuous measurement of the status of the efficacy of catheters, such as catheters in a brain ventricle, a multi-microsensor system is disclosed that monitors various hydrodynamic shunt variables and includes non-invasive wireless data communication to report on shunt status. These hydrodynamic variables include, but are not limited to, intracranial pressure (ICP), differential pressure across the shunt, shunt CSF flow, and catheter patency.

To determine these variables, one approach is to utilize sensing methods based on electrochemical impedance monitored between thin film electrodes. For example, to detect pressure, a pair of electrodes may be used to track changes in electrochemical impedance induced by the instantaneous size change of a microbubble in response to local pressure changes. Differential pressure measurements can be made across a shunt by placing sensors near the ends of the shunt. Flow measurements can be obtained by perturbing the electrochemical impedance of the flowing fluid. For example, fluid near a microfabricated heater can be transiently heated and the resulting heat pulse's time of flight recorded via electrochemical impedance measured at one or more electrode pairs. Another possibility is to generate a microbubble via electrolysis and record the resulting impedance spikes downstream at one or more electrode pairs. For patency measurement, electrodes may be situated internal and external to the perforated proximal catheter and monitor blockage of the ionic conduction path by tissue, blood, or other debris. Advantages of using the electrochemical impedance transduction method over other conventional sensing principles may include low power operation, simple sensor design, and fabrication, and compact footprint.

Figure 1:
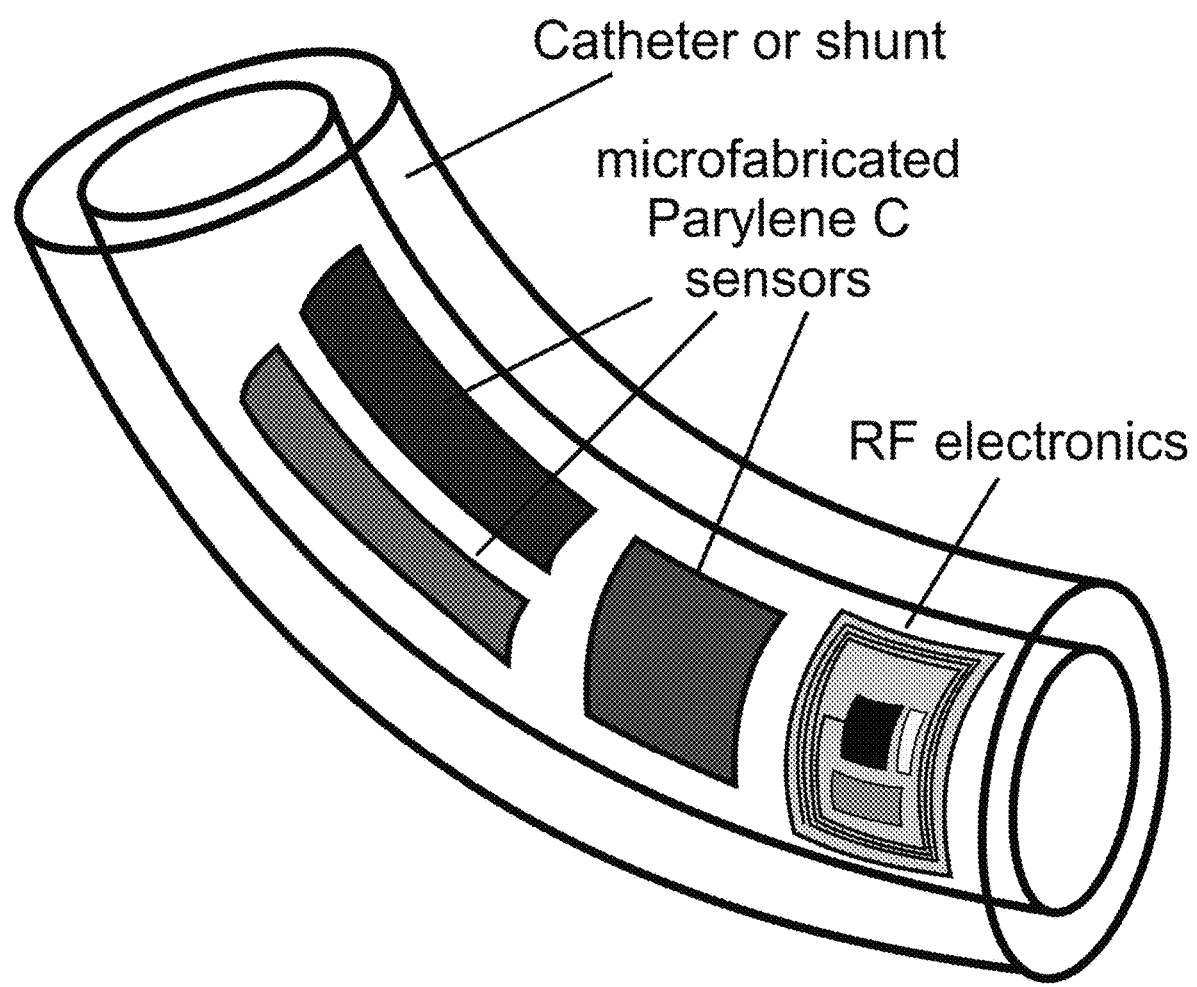
FIG. 1 illustrates an example of a multi sensor platform placed within the lumen of a catheter or shunt.
Figure 2:
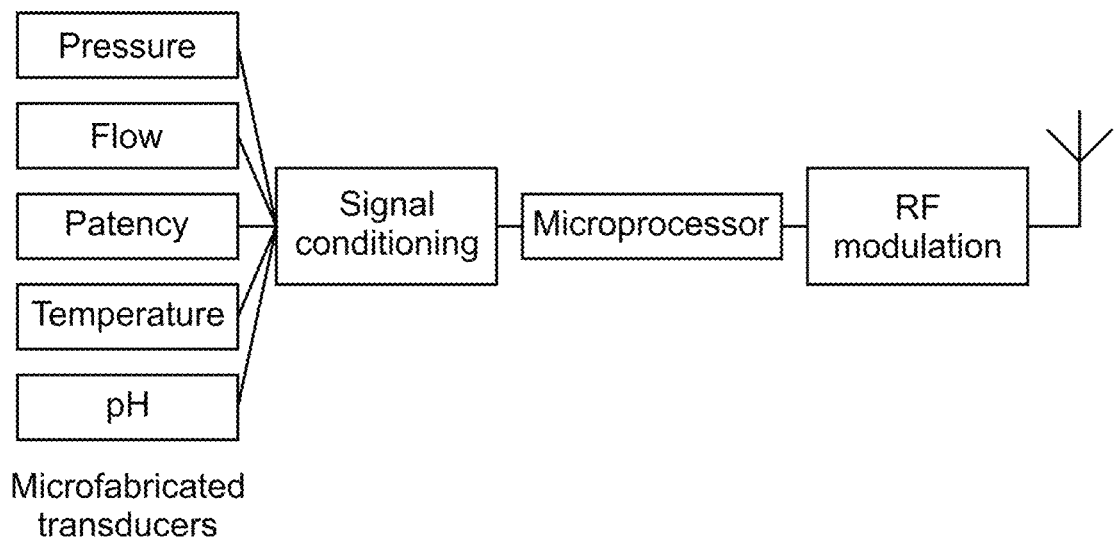
FIG. 2 illustrates an example of a combination of sensors for an implantable multi sensor system with wireless telemetry.

Pressure, flow, and patency sensors may use microfabrication technology so that they can be miniaturized for integration with a shunt. In a representative embodiment, sensors were co-fabricated on a single flexible polymer (Parylene C) substrate to form a single multi-sensor module. The sensor output can be connected to a microprocessor or similar circuitry that performs the functions of data acquisition, signal processing, and wireless telemetry. Data and power can be wirelessly transmitted from the implanted sensor module using inductively linked coils. The information obtained can be passed to a user interface that allows display of sensor outputs such as pressure, flow, and patency (e.g., FIGS. 1, 2 & 3).

Integration of these sensors individually or in multi-sensor modules with current catheter technologies may allow for rapid and accurate diagnosis of shunt failure and thus initiate timely intervention to avoid prolonged suffering of hydrocephalus patients. In addition, because of the thin film construction and simple transduction methods, these sensors can be used together or individually for a broad spectrum of catheter diagnosis applications for any fluidic drainage interface (e.g. intravascular, intraocular, intra-abdominal, etc.).

General Description

An implanted multi-sensor system chronic monitoring of the status of implanted drainage catheters is disclosed. The implanted system may wirelessly communicate sensor data as a means of early and definitive detection of shunt failure. One embodiment of the system may use microfabricated sensors that can track relevant hydrodynamic parameters by electrochemical impedance measurements. These hydrodynamic variables may include, but may not be limited to, intracranial pressure (ICP), differential pressure across the shunt, shunt CSF flow, and catheter patency. Three microfabricated sensors for measuring pressure, flow, and patency were built.

The sensors may all utilize electrochemical impedance transduction in which the sensing electrodes are directly exposed to the CSF and are therefore simple in construction. The open architecture format may obviate the need for complex hermetic packaging or other forms of sensor encapsulation. They may share in common the same materials for the structural layers and electrodes. Therefore, these sensors can easily be integrated on the same substrate. One such substrate is a flexible polymer that permits facile application to current shunts, either as a modular add-on or directly incorporated into a shunt. By having different sensors to track three different metrics of interest for shunt status, each measurement can provide a different aspect of shunt efficacy (e.g. shunt efficacy in measuring flow, shunt state in measuring patency, and a combination of both in measuring ICP) as well as provide redundancy in assessing the shunt state. All three sensors were fabricated on a single Parylene C substrate with thin film platinum as the traces and electrode sites for each sensor. A brief description of each sensor and the sensing mechanism is now presented.

Figure 4:
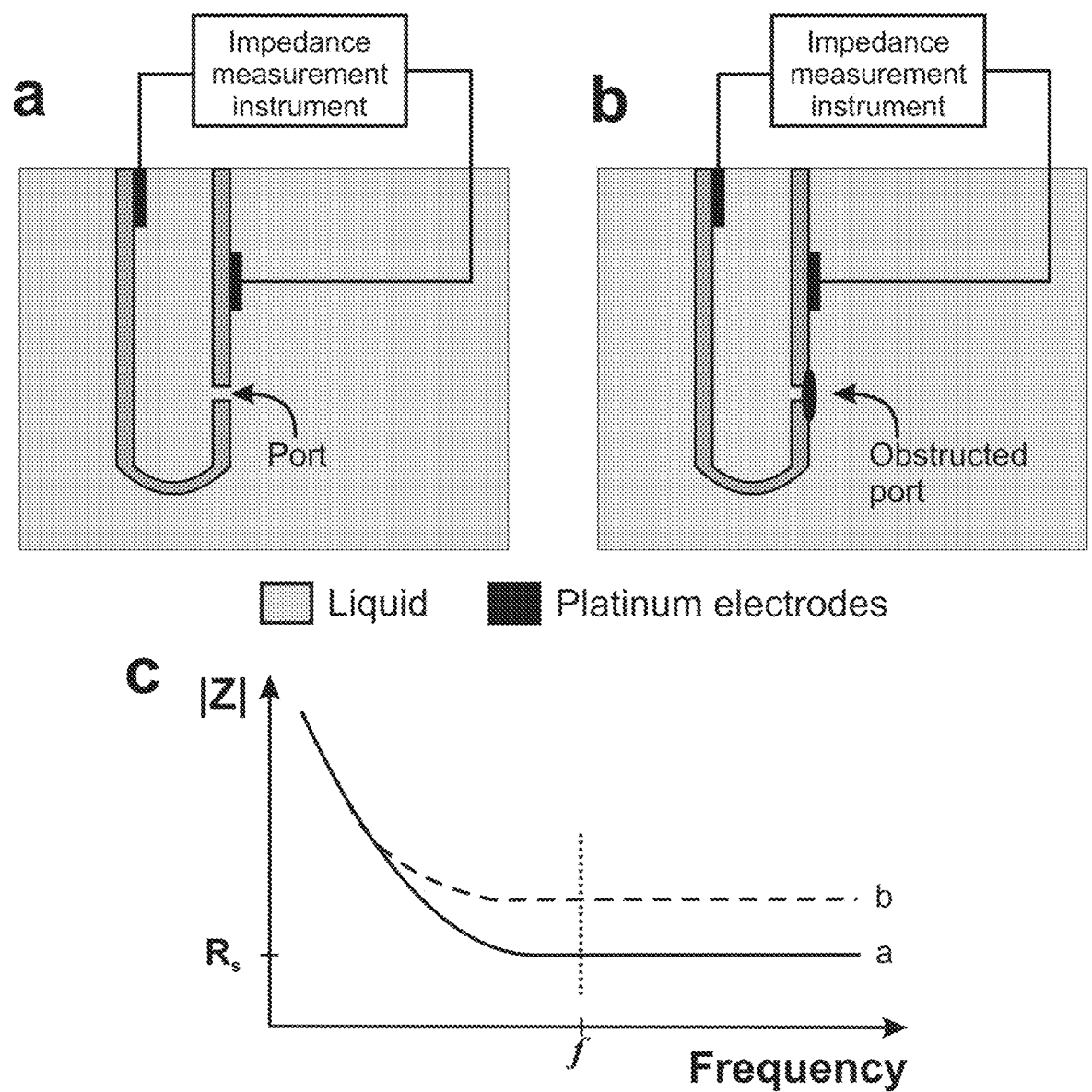
FIGS. 4A-4C illustrates an example of impedance-based tracking of catheter obstruction.
Figure 5:
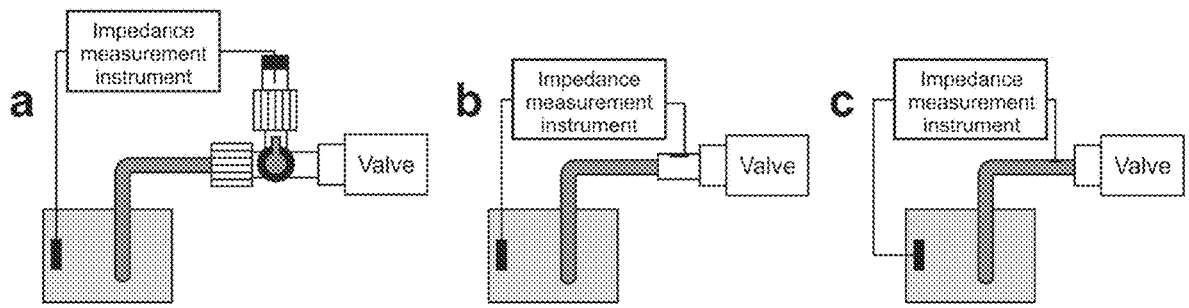
FIGS. 5A-5C illustrate examples of possible orientations of a sensor for use in catheter systems. Because of the thin film construction of the sensor, the device can be placed within modular units that are adjacent to (FIG. 4A) or inline with (FIG. 4B) the valve unit. The sensors may be integrated within the catheter itself, as shown in FIG. 4C.

Details of the mechanisms of an example patency sensor are given in provisional patent No. 62/046,424, but are present here for completeness. Briefly, patency may be measured by a pair (or more) of measurement electrodes: one set on the internal surface of the catheter, and one on the external; these electrodes may share a fluidic path via the drainage ports of the catheter (FIG. 4). Any number and orientation of electrodes may be included in the inner or outer surface to increase device performance. Changes in impedance measured through the fluid may be produced by the obstruction of these ports by cellular debris and tissue (FIG. 4). The electrochemical impedance of the solution spanning the two immersed electrodes may be monitored and an increase in impedance due to port blockage can be measured.

Details of the mechanisms of an example pressure sensor are given in U.S. Pat. No. 8,490,497, but are presented here for completeness. Briefly, the electrochemical impedance-based pressure sensor may operate using pressure-induced variations in microbubble size, measured via fluctuations in electrochemical impedance. The pressure sensor may include a Parylene C microchannel that encloses two pairs of electrodes. One pair of electrodes (hereon referred to as the "electrolysis electrodes") may sit within the main channel of the microchannel structure, or within a separate compartment of the channel known as the "nucleation core." This pair of electrodes may be responsible for generating the pressure-sensitive microbubble using an electrolytic process. If the electrolysis electrodes are placed within the separate nucleation core, bubble guiding structures may also be present to allow for the formed microbubble to situate itself within the main channel; for electrolysis electrodes that are already present in the main channel, the guiding structures may not be necessary. The formed microbubble may sit between the second pair of electrodes (hereon referred to as the "measurement electrodes") that measures the impedance between them. The microbubble may influence the volumetric conduction path between the measurement electrodes, and any changes in microbubble size (induced by changes in pressure) may generate corresponding changes to the measured electrochemical impedance.

Bubble gating structures, or other design specifics, may also be present to ensure that the bubble remains between the measurement electrodes. In some designs, both functions (i.e. electrolysis and measurement) are may be accomplished using a single pair of electrodes.

Flow sensing may be achieved by monitoring perturbations of the flowing material's electrochemical impedance (EI). Two methods to perturb the EI were implemented and characterized: heat and phase change. First, a heat pulse may be first generated by a microfabricated heater composed of a serpentine platinum trace insulated on both sides by a thin Parylene C film. At least one pair of platinum electrodes may be placed a known distance away from the heater parallel to the direction of flow. To measure flow rate, the heated material may be monitored as it flows past the electrode pair and registers as a drop in electrochemical impedance with a magnitude proportional to the temperature of the fluid. Since the distance between the heater and impedance monitoring electrodes may be known, flow may be calculated from separation distance and the transit time of the heated material from the heater to the monitoring electrodes. This is referred to as the time of flight mode.

If the impedance electrodes are close to the heater such that diffusion is the primary means of heat transfer, the flow rate can be measured via the rate of change in temperature, where faster flow rates cause the temperature at the electrodes to increase more rapidly than with slower flow rates. If the electrodes are farther away such that convection is the primary means of heat transfer, a time of flight mode may be used. Using multiple sensing electrode pairs may add to the accuracy of time of flight measurements by allowing a heat pulse to be tracked past multiple points.

A calorimetric method of flow measurement may also be used where the fluid is heated constantly and the steady-state temperature at an electrode pair a known distance away is correlated with flow rate. In all methods of operation, this flow sensor may be more sensitive and more efficient than current state of the art flow sensors, since the flowing material's impedance may typically have a temperature coefficient an order of magnitude higher than conventional temperature-dependent resistors.

Alternatively, electrochemical impedance can be perturbed by introducing one or more electrolytically generated microbubbles and tracking the time of flight past two pairs of measurement electrodes at a set distance from one another, utilizing this time of flight mode to calculate the flow rate. This TOF flow sensor may include three pairs of linearly arranged electrodes, one pair to form the microbubble which serves as the flow indicator ("electrolysis electrodes"), and the other two pairs to measure the points in time at which the microbubble travels across two specific positions using electrochemical impedance ("measurement electrodes").

The electrolysis electrodes may be used to generate a microbubble of a sufficient size to travel across and be detected at the two measurement sites. Passage of the microbubble through each pair of measurement electrodes may register as an increase in impedance (impedance spike). Each pair of measurement electrodes may initially measure a baseline impedance until the microbubble disrupts the conduction pathway and produces a measured impedance spike in time. By knowing the distance between the two positions, and the time it took for the microbubble to travel from one point to the other, the flow rate can be calculated from the impedance spike data obtained from the measurement electrodes.

To further guide the bubble towards the measurement electrodes, physical guidance structures (such as guide rails or etched grooves) can be used. Alternatively, bubble generation may be guided towards the sensing electrodes using a structure such as a nucleation core [L. Yu and E. Meng, "A microbubble pressure transducer with bubble nucleation core," in *Micro Electro Mechanical Systems (MEMS)*, 2014 *IEEE 27th International Conference on*, 2014, pp. 104-107.]. Guidance structures are optional to enhance performance and may not be needed.

For the impedance measurements between the measurement electrodes in all three sensors, the electrode-electrolyte interface may be modeled by the Randles circuit which may include the solution (electrolyte) resistance in series with the parallel combination of the double layer capacitance and polarization resistance. Measurement of electrochemical impedance may be accomplished by applying a low frequency (typically in the 1-50 kHz range) AC voltage across the electrodes. At such frequencies, the impedance response may be dominated by the solution resistance. The voltage selected may be low such that only reversible chemical reactions are present and the solution is not chemically modified during the measurement process. Several techniques may be available to measure electrochemical impedance but this may be done with an external measurement instrument, such as an LCR meter or impedance/network analyzer. This kind of measurement may consume very low power, such as requiring only nW-µW (1-100 mV, 1-100 nA).

Figure 3:
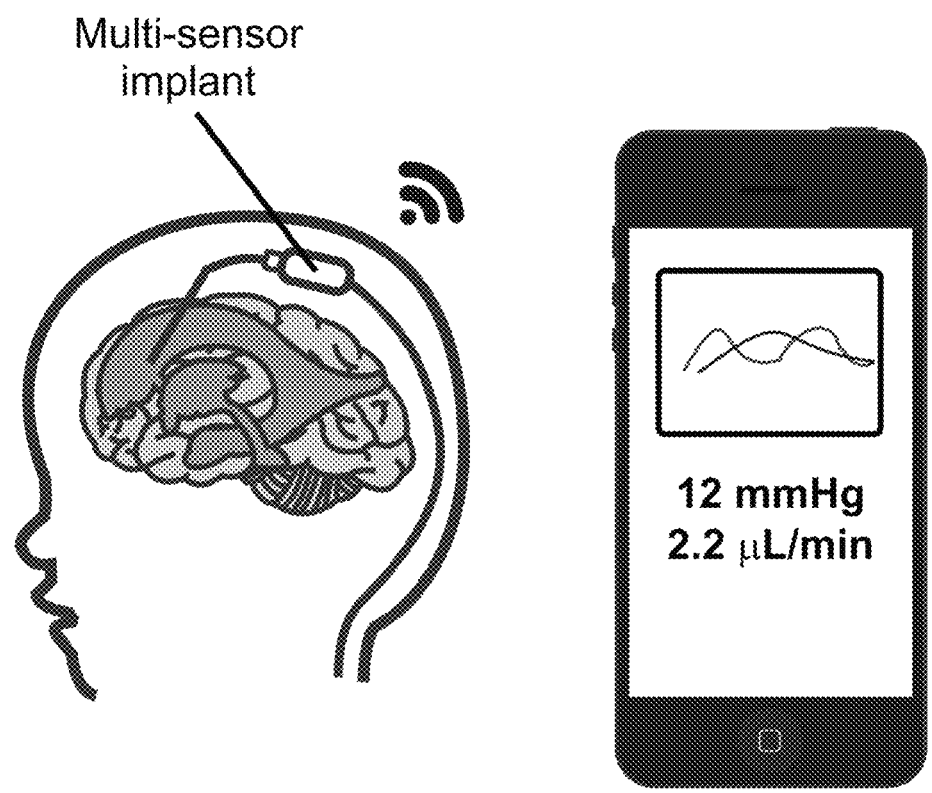
FIG. 3 illustrates an example of a multi-sensor implant within a hydrocephalus shunt, with wireless communication to an external graphical user interface.
Figure 6:
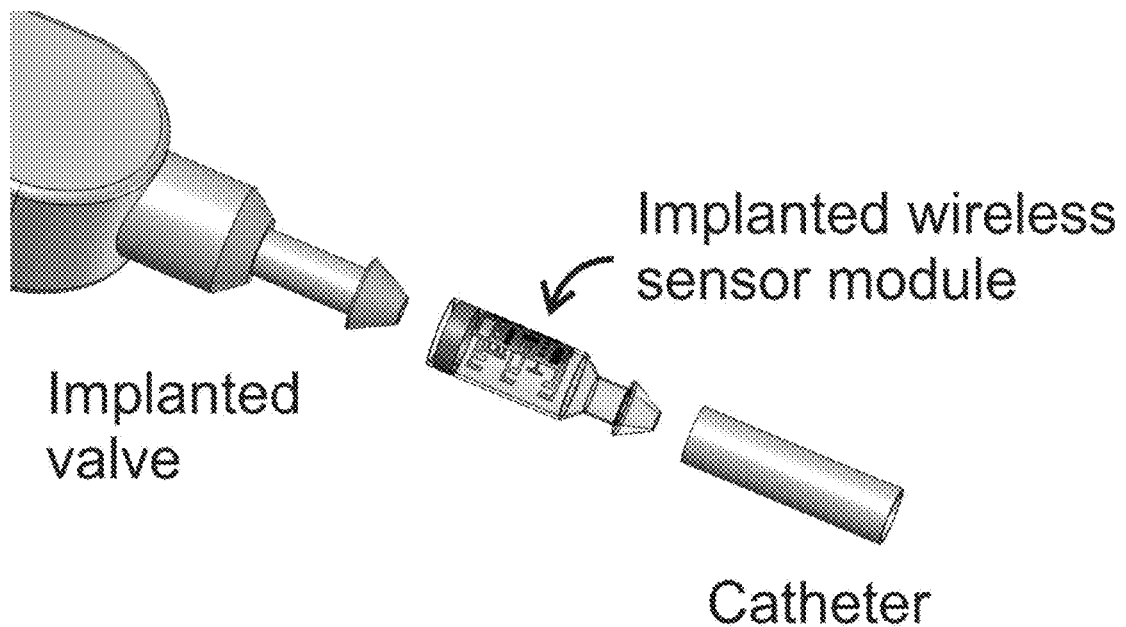
FIG. 6 illustrates an example of a sensor module orientation for an implanted catheter system.

As these electrodes and sensors are built on a polymer substrate, they can be oriented in different configurations: such as, part of a modular system that can be attached and removed from existing systems (either inline or adjacent) or built into the catheter itself (FIG. 6). If implanted within the body, wireless impedance measurement techniques (circuitry) can also be included to allow for wireless data and power transmission (FIGS. 3 & 6). Non-limiting examples of the system application includes other shunts (cardiac, cerebrospinal, cerebral, pulmonary), catheters (Quinton, Swan-Ganz, urinary, vascular), and medical ports (arterial, vascular). Other examples of usage include drug delivery devices, stents, subcutaneous sensors, artificial prosthetics, mechanical heart valves, contact lenses, and the like.

Prior to combining all sensors onto a single substrate, each sensor was fabricated separately and was tested on benchtop. The results of testing is now described.

Figure 8:
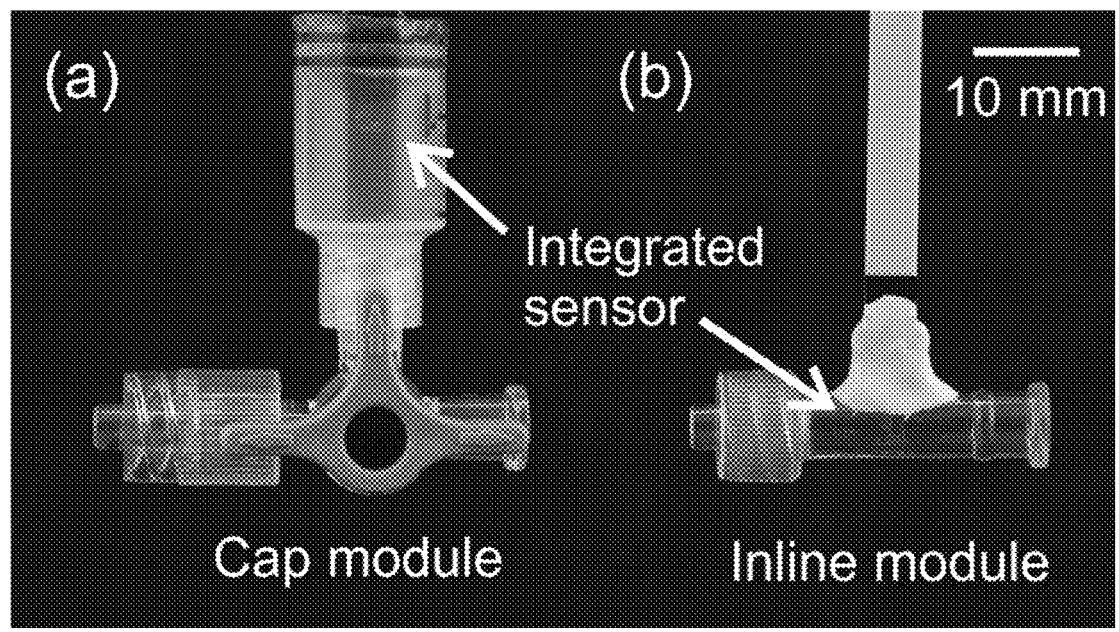
FIG. 8A illustrates an example of an assembled cap and FIG. 8B illustrates an example of inline modules for simple integration of a Parylene-based patency sensor with external ventricular drains within a clinic using standard luer lock connectors.

A Parylene-platinum thin-film patency sensor was integrated with a mock catheter for proof-of-concept testing. The sensor was fabricated on a silicon carrier wafer by using standard microfabrication methods for Parylene-based devices. To allow for fluidic coupling between the sensor and the mock catheter, two modules were created to allow for proper integration: a cap module and an inline module (FIG. 8). To construct the cap module, the patency sensor was first electrically connected to a commercial available zero insertion force (ZIF) connector with a flat flexible cable end, and then was affixed within a slit of a rubber stopper cap attached to the top of a module. The module was then filled with artificial CSF (aCSF).

A 3-way valve system allowed for simultaneous attachment of the module, mock catheter (silicone), and syringe/pump to allow for fluidic interconnect between all three components. To construct the inline module, following proper packaging of the patency sensor using the aforementioned process (ZIF connector and flat flexible cable), the assembly was affixed within a slit in a female to male luer lock adaptor. The assembly was affixed using biocompatible USP Class VI epoxy. Because of the design of the inline module, a 3-way valve system was not necessary, which allowed for direct connection of the inline module to the mock catheter and syringe/pump system.

Figure 9:
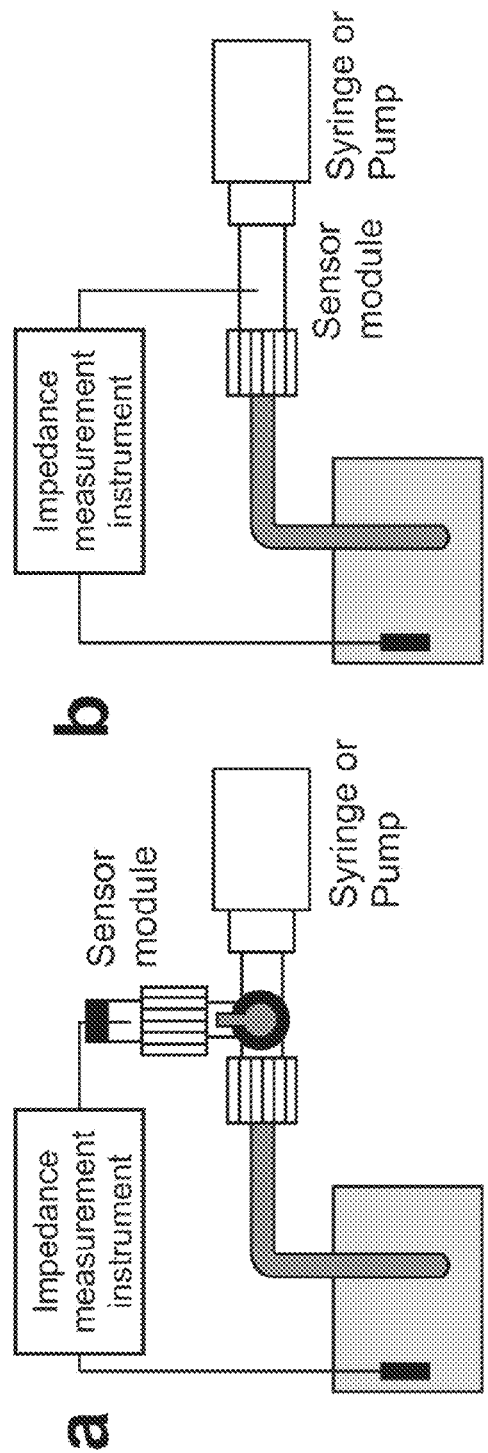
FIGS. 9A-9B illustrate examples of a testing setup for experiments of the Parylene-platinum thin-film catheter patency sensor.
Figure 10:
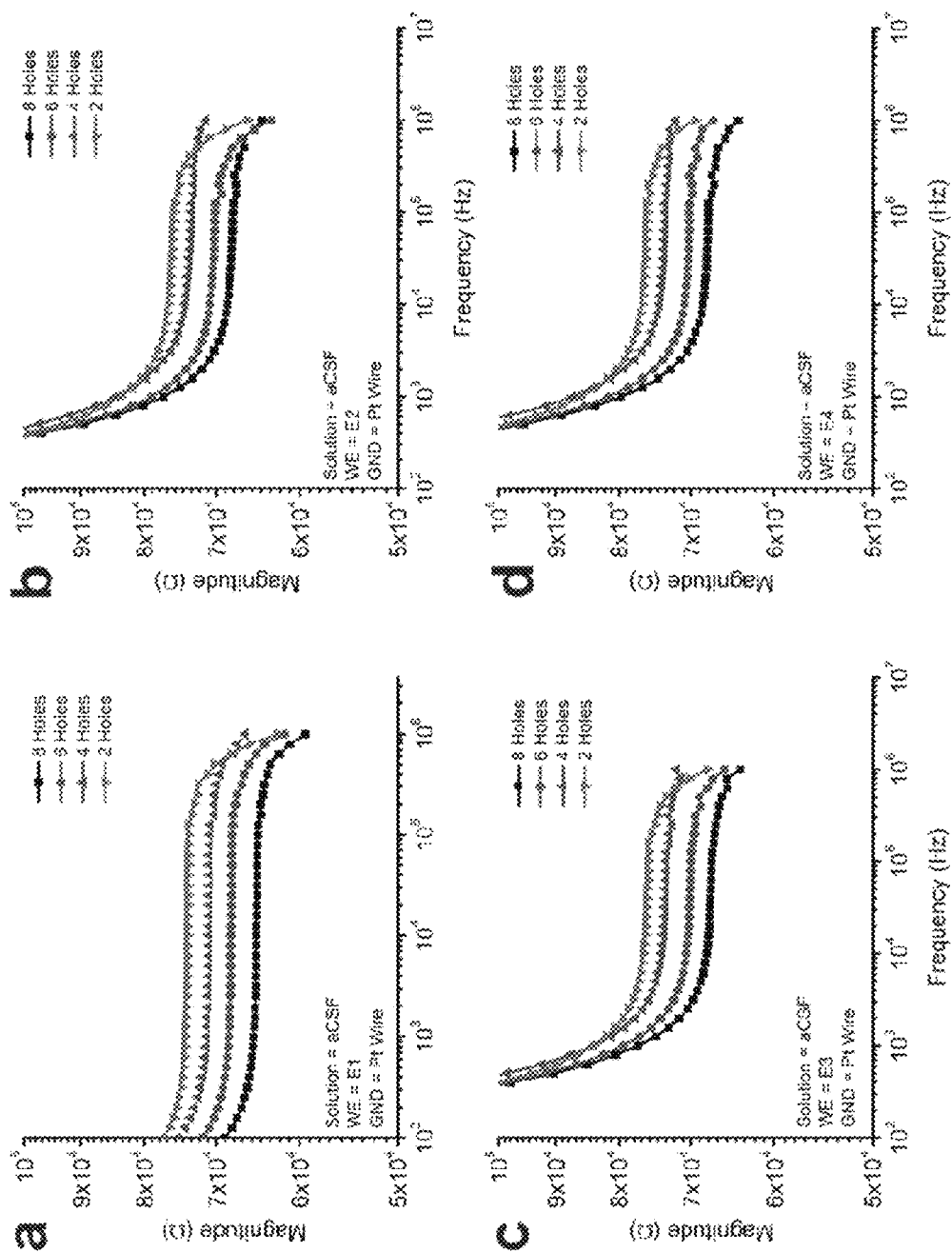
FIGS. 10A-10D illustrate examples of impedance responses of varying catheter blockages (2, 4, 6, 8 holes) for four electrode sizes: E1 (FIG. 10A), E2 (FIG. 10B), E3 (FIG. 10(C), and E4 (FIG. 10D). A cap module was used for testing.

Blockage of the catheter was simulated by constructing mock catheters with varying numbers of holes with 16 holes being 100% open; thus a 2 holed catheter would be classified as 87.5% blockage, 8 holes as 50%, and 4 holes as 25%, etc. The catheter was then placed within a beaker of aCSF and filled via the syringe or a peristaltic pump, and a corresponding platinum wire electrode was also placed within the beaker for completion of the sensing setup. Impedance measurements were acquired using a potentiostat (Gamry R600; 25 mV$_{RMS}$, 0.1-1E6 Hz) for three-point impedance measurements or a high precision LCR meter (Agilent e4980a or Agilent 4285a) for two-point impedance measurements connected to the impedance measurement electrodes (FIG. 9).

Figure 7:
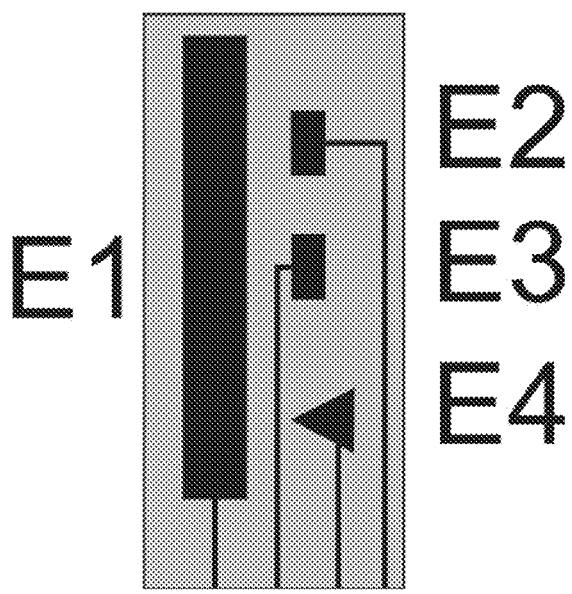
FIG. 7 illustrates an example of platinum electrodes patterned onto a Parylene substrate for initial patency sensor testing. The comparative surface areas of the electrodes may be such that E1>E2=E3>E4.
Figure 11:
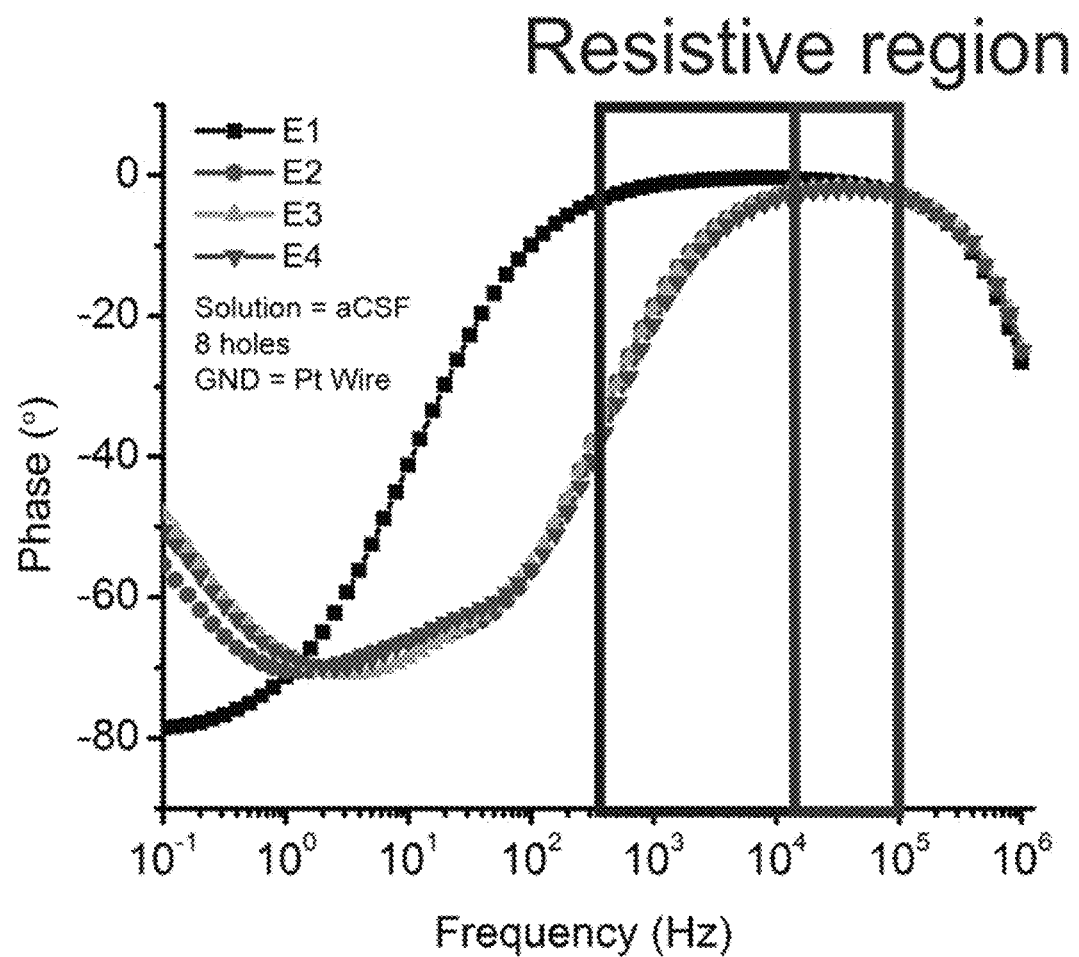
FIG. 11 illustrates an example of results of a two-point electrochemical impedance spectroscopy to determine the resistive region, and corresponding $f_{measurement}$ to isolate the solution resistance for best sensing capability. The small blue square within the black outline indicates the resistive region for smaller electrode sizes (E2-E4). A cap module was used for testing.
Figure 12:
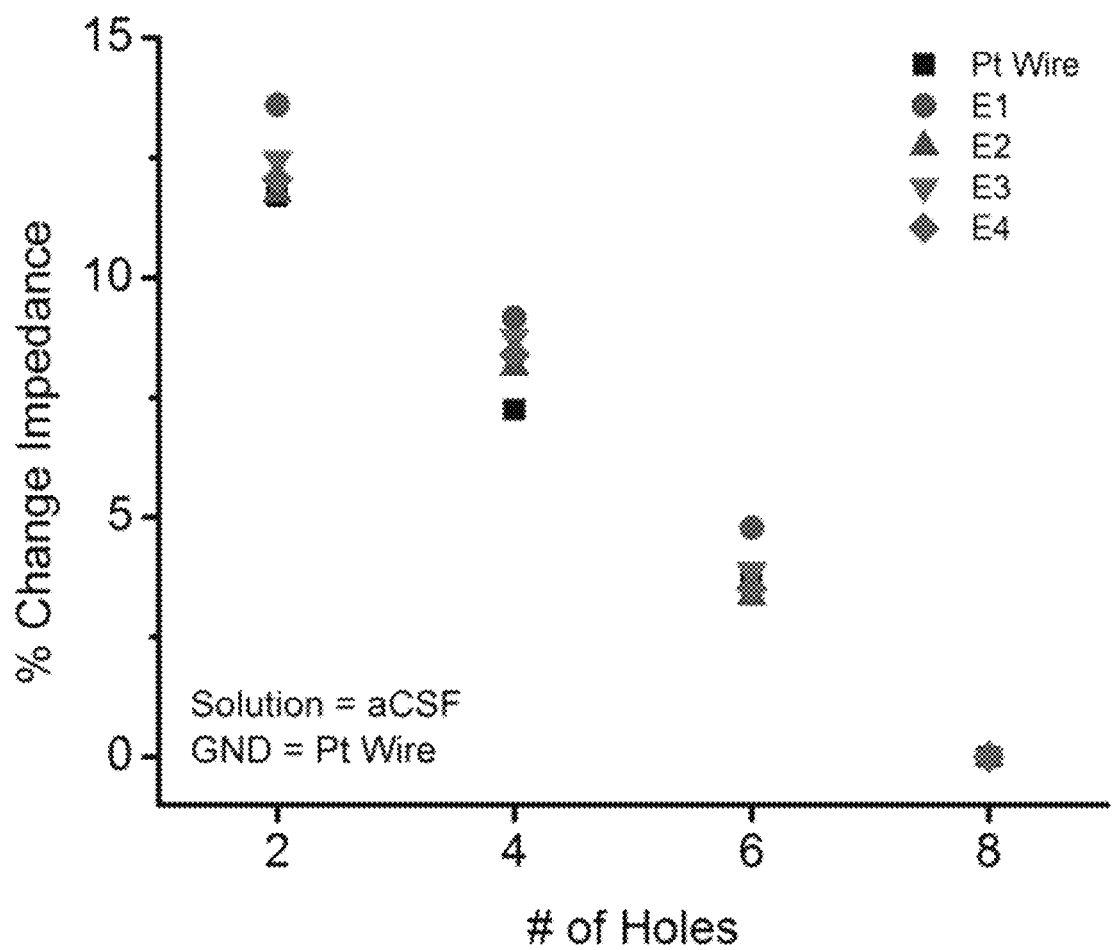
FIG. 12 illustrates an example of a calibration curve obtained for each of the different $f_{measurement}$ for the various sensing electrodes (a bulk Pt wire included), indicating a fairly linear impedance-obstruction response for mock catheters up to 8 holes using the cap module.

Initial tests were conducted at frequency ranges of 0.1-1 Mhz, and found that the impedance over specific frequency ranges (corresponding to where the solution resistance dominates the impedance response, i.e. the resistive region) correlated well with catheter blockage over varying electrode sizes and types (FIG. 7). Two-electrode electrochemical impedance spectroscopy was then performed to determine the optimum frequency at which solution resistance dominates the impedance response (FIG. 11). For aCSF, the measurement frequency (fmeasurement) was found to be different depending on the electrode size ranging from 10-30 kHz. Following this, a calibration curve was created for these frequencies for the different electrode sizes, and indicated that the impedance varied quite linearly with the percent blockage of the catheter for blockages between 50-87.5% (FIG. 12).

Figure 13:
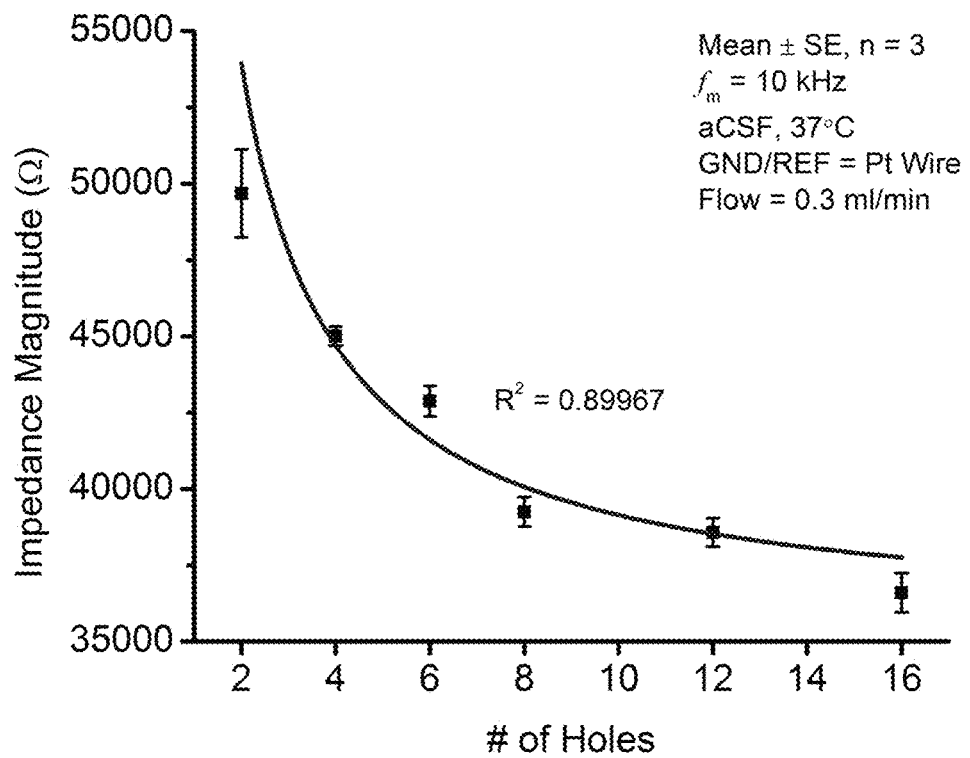
FIG. 13 illustrates an example of a calibration curve for E1 sensor indicated that as the number of holes opened increased to 16 (full calibration), the response of the sensor was more inversely proportional, increasing in sensitivity as the catheter becomes more blocked. A cap module was used for testing.
Figure 14:
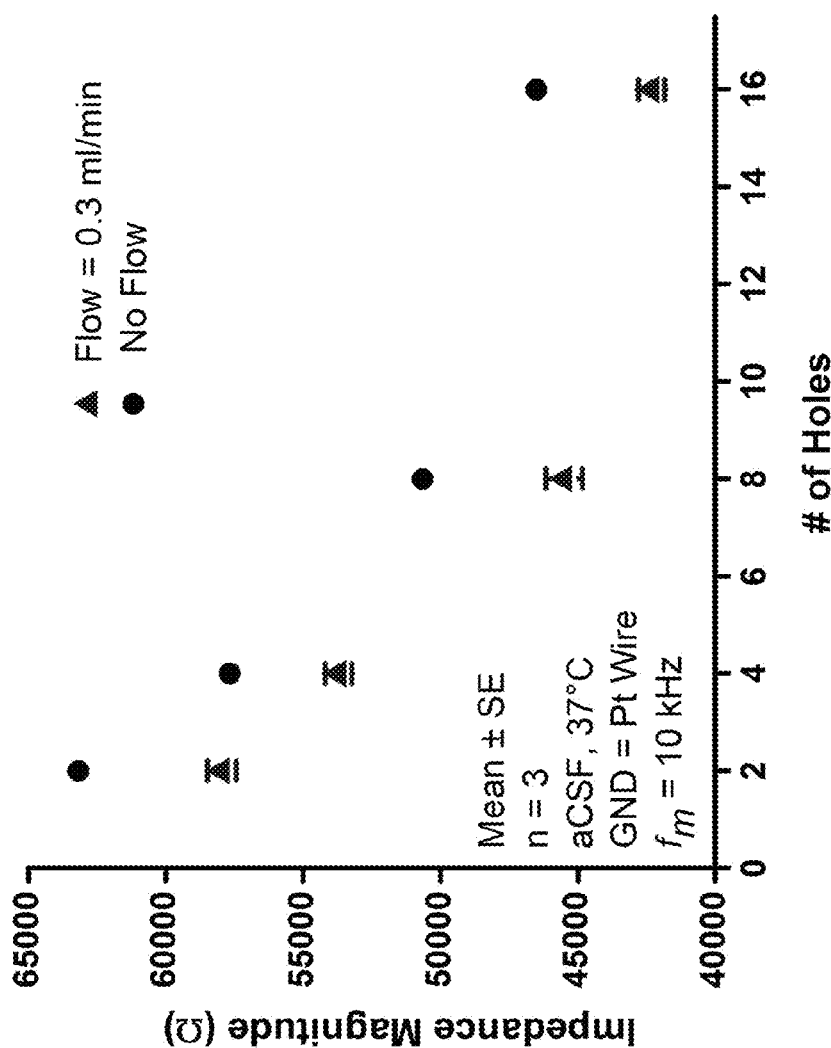
FIG. 14 illustrates that sensor performance can in no flow and flow conditions indicate that, though the baseline impedance is reduced, the functionality of the sensor is maintained. A cap module was used for testing.
Figure 15:
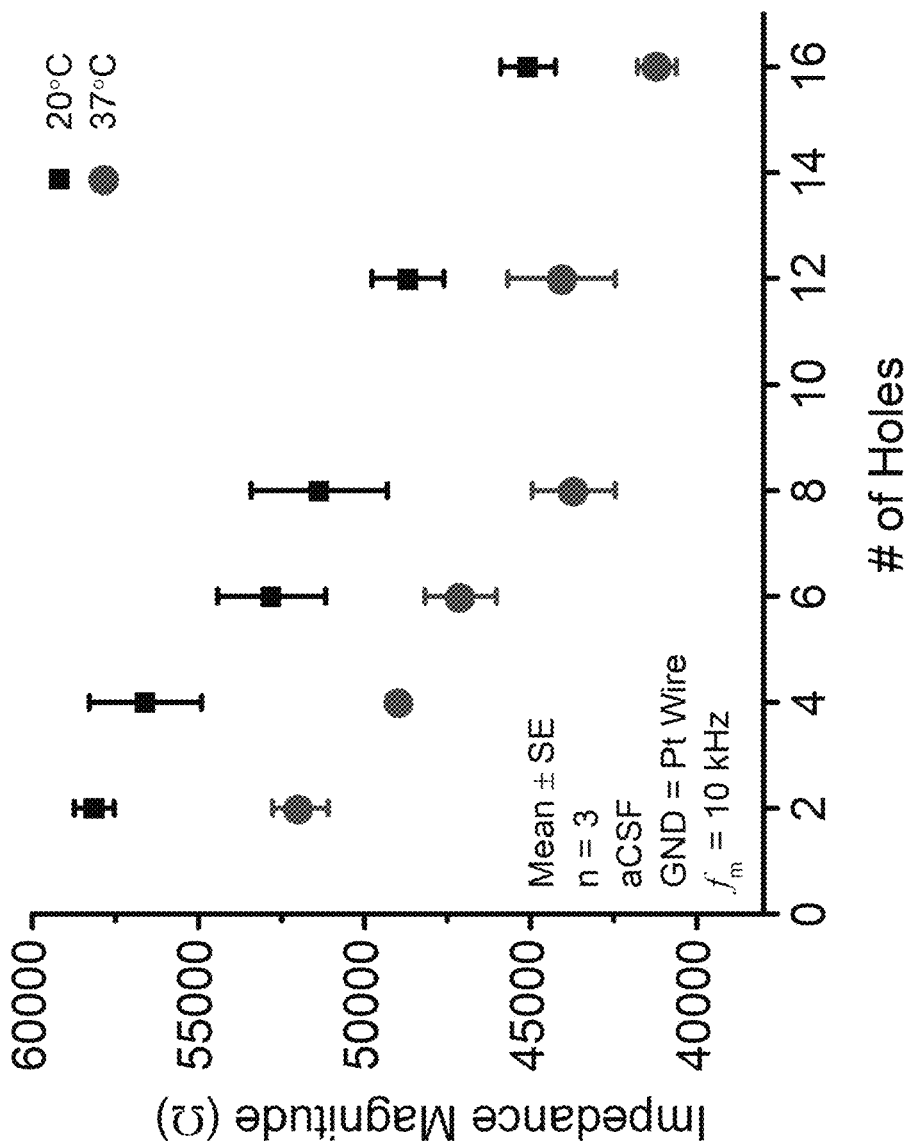
FIG. 15 illustrates that sensor performance at body temperature compared to room temperature can also indicate a decrease in baseline impedance, but the functionality of the sensor is still maintained. A cap module was used for testing.
Figure 16:
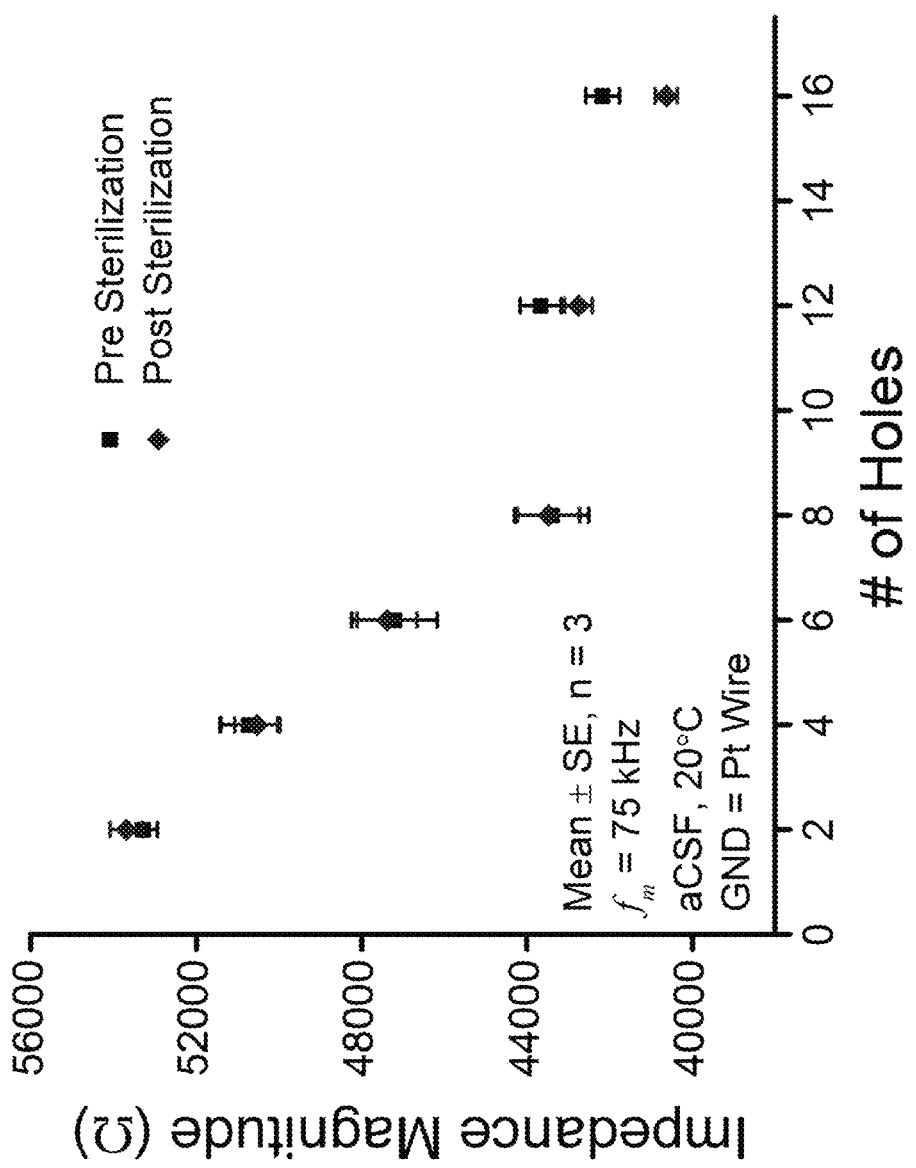
FIG. 16 illustrates that sensor performance following $H_2O_2$ plasma sterilization can indicate that functionality was still maintained following sterilization.
Figure 17:
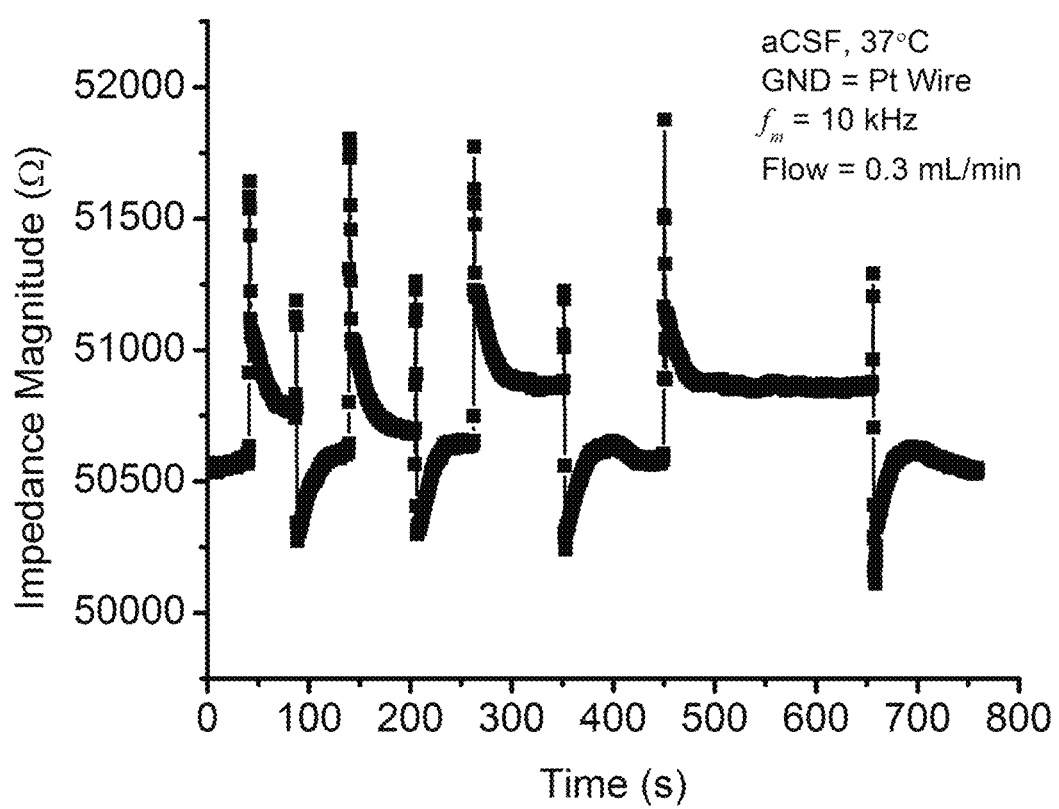
FIG. 17 illustrates that sheathing/unsheathing experiments of a 16 hole catheter to simulate dynamic blockage illustrated the real-time measurement capabilities of the Parylene patency sensor in measuring shunt patency. A cap module was used for testing.

Results indicated that the impedance varied inversely with the percent blockage of the catheter (in the total range of 0-87.5%), demonstrating a 27% impedance increase for ~87% blockage (FIG. 13). Sensor operation at 37° C. and under flow conditions (using the peristaltic pump at 0.3 ml/min) indicated a decrease in baseline impedance for both conditions, but functionality was still maintained (FIGS. 14 & 15). $H_2O_2$ plasma sterilization of the sensor module also had no large effects on sensor functionality (FIG. 16). The ability for the sensor to capture dynamic blockages simulated by sheathing/unsheathing the catheter was also confirmed (FIG. 17).

Figure 18:
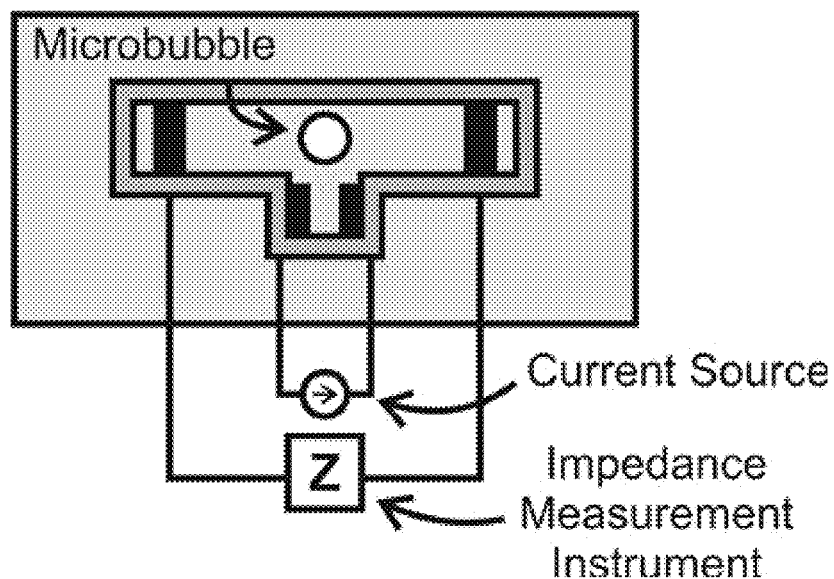
FIG. 18 illustrates an example of a microbubble pressure transducer. A pair of electrodes on either side of an electrolysis induced microbubble tracks the electrochemical impedance changes caused by the instantaneous response of the bubble to pressure changes.

A microchannel-based microbubble pressure transducer (μBPT) with microbubble nucleation core (μBNC) was developed for characterization of microbubble dynamics and pressure transduction in wet environments (FIG. 18). The transducer leverages electrochemical impedance (EI)-based measurement to monitor the instantaneous response in size of localized microbubbles (μBs) induced by hydrostatic pressure changes (−93 Ω/mmHg sensitivity over 0-350 mmHg). Repeatable, efficient generation of stable microbubbles (<1.5 nL with <2% size variation) was achieved by electrolysis using a μBNC structure adjacent to the microchannel center. Biocompatible construction (only Parylene and Pt), low power consumption (<60 μW), and liquid-based operation of μBPTs are well suited for chronic in vivo pressure monitoring.

The μBNC consists of a pair of closely-spaced microelectrodes (50 μm apart) enclosed within a tapered cavity directing bubbles into the adjacent microchannel. Typically, nucleation via electrolysis creates μBs within natural microcavities randomly distributed on the electrode surface; the cavity structure of the μBNC forces μBs to coalesce before entering the microchannel. When the μB spans the microchannel (~200 μm wide), termination of electrolysis current results in μB detachment from the μBNC. The measurement microelectrodes situated at the ends of the microchannel around the μB (1000 μm apart) can now be used for EI-based pressure measurement. Gating structures in the microchannel confine μBs within the measurement area and prevent escape through the open-ended channels. The μBPT was fabricated on a flexible Parylene C substrate with Pt electrodes.

Localized and metered bubble nucleation were demonstrated. Microbubbles were electrolytically generated in 1× PBS (<4 μA, 5-25 s) at the μBNC and consistently exited into the measurement channel; bubble size was quantified optically and with EI measurement. Electrochemical impedance spectroscopy yielded 10 kHz as the optimum frequency (minimum system phase) for maximizing the solution resistance component of the impedance response. Power draw was ~1 nW for EI measurement (1 Vp-p) and <60 μW for electrolytic bubble generation. The gas evolved from electrolysis of PBS is nearly all hydrogen. From the injected current, three types of μBs were observed: type I μBs were confined in the μBNC (<16 μC); type II spanned both the μBNC and microchannel (16-40 μC); type III resided in the microchannel, detached from the μBNC (>40 μC). Pressure transduction was performed only for type III μBs. Type I and II As had short lifetimes (<5 s) due to H2 contact with Pt electrodes, which catalyze recombination. Type III μBs maintained constant size (>15 min) due to diffusion-limited dissolution. High precision EI measurement (SD <2% of mean) of bubble size was achieved.

Figure 19:
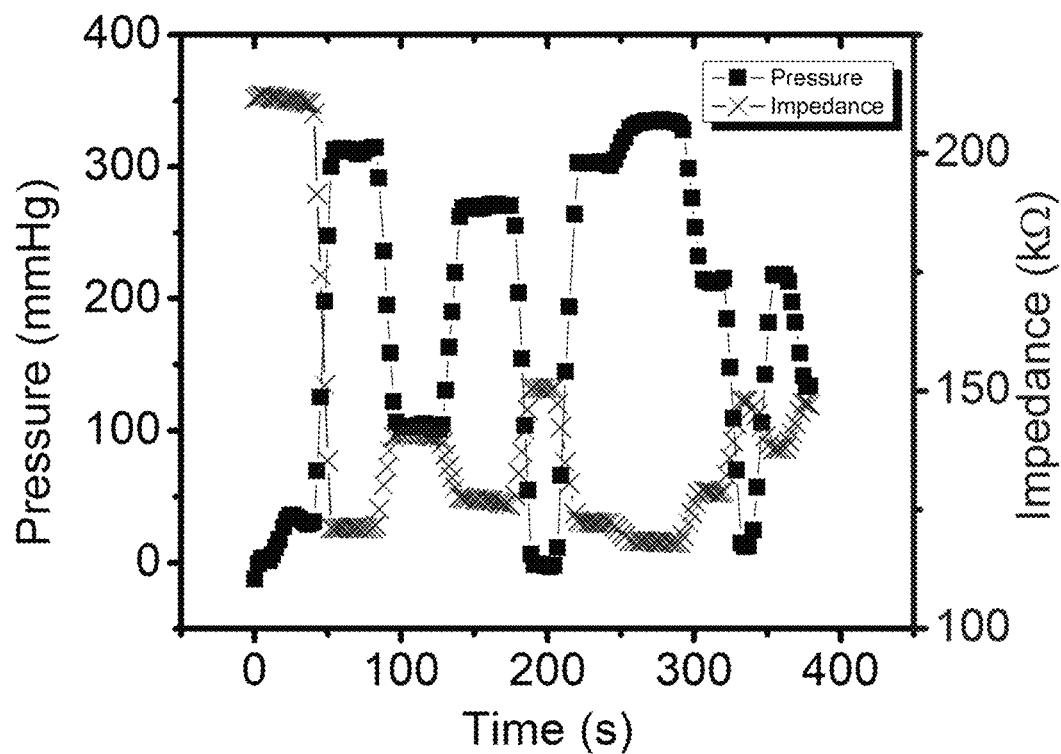
FIG. 19 illustrates an example of real time tracking of pressure with a microbubble pressure transducer. Increased pressure may induce compression of microbubble, lowering solution resistance. Decreased pressure may cause microbubble expansion and increased impedance.
Figure 20:
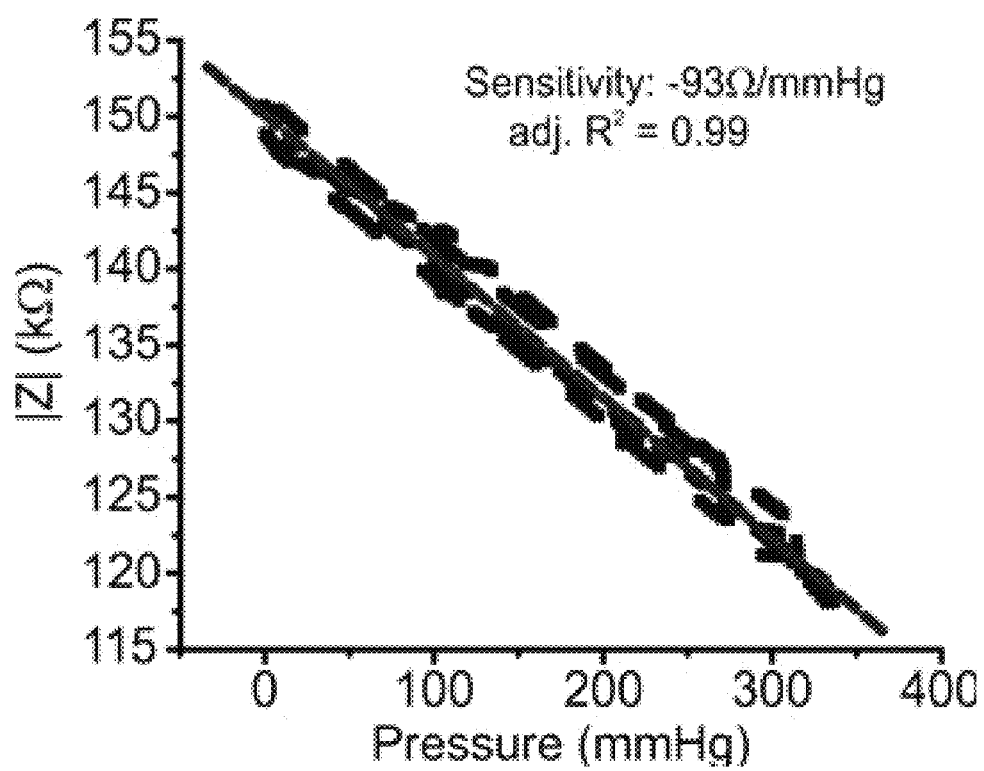
FIG. 20 illustrates an example of impedance-pressure correlation that illustrates sensitivity of microbubble pressure sensor. The highly linear response suggests that bubble size is directly proportional to applied pressure.

Hydrostatic pressure measurement used a calibrated pressure source attached to a custom test fixture housing the μBPT. A μB was generated at 0 mmHg; subsequent pressure oscillations were tracked in real-time (FIG. 19). A linear trend between EI and applied pressure was observed, yielding a sensor response of −93 Ω/mmHg (FIG. 20). Further sensor characterization is underway (varying electrolyte composition, temperature, pH, μBNC geometry).

A microfabricated flow sensor which utilizes the flowing material's electrochemical impedance to measure the effects of flow rate on a generated heat pulse was developed and tested. Biocompatible construction using platinum traces on a flexible Parylene C substrate enables unobtrusive insertion into medical implants such as shunts and catheters. The sensing principle uses electrochemical impedance measurements between an electrode pair to sense temperature changes produced by an upstream heater, which may offer increased sensitivity and compatibility in saline environments. Initial prototypes detected flow rates less than 160 μL/min with a limit of detection (LOD) of 10.7 μl/min. The simple design may be ideal for extended in vivo applications.

Figure 21:
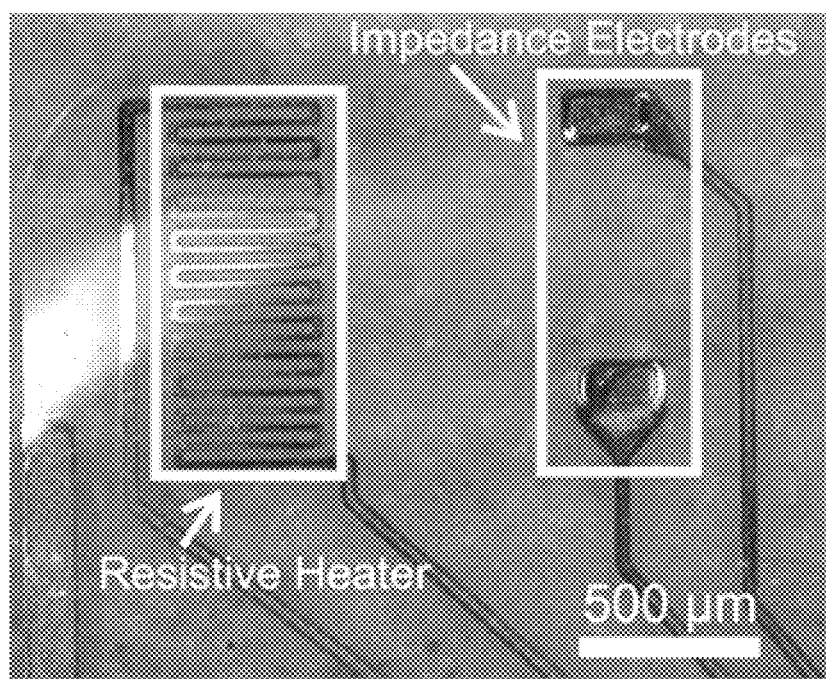
FIG. 21 illustrates an example of a flow sensor fabricated with platinum traces on a Parylene C substrate. The heater may include a snaked platinum trace, while temperature may be sensed by a pair of electrodes.
Figure 22:
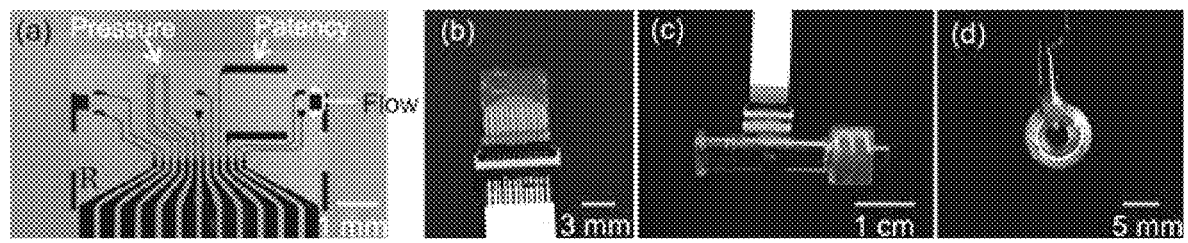
FIG. 22A illustrates an example of sensors constructed of thin film platinum electrodes on a single Parylene C polymer substrate.
FIG. 22B illustrates an example of a commercial zero-insertion force (ZIF) connector to electrically connect to the sensor platform.
FIG. 22C illustrates an example of a sensor platform incorporated (via curling (FIG. 22D)) into a luer lock compatible module for connection to a commercial external ventricular drain (EVD) catheter system that may be eventually used as a validation module in human subjects.

The impedance of ionic solutions decrease with increased temperature due to increased ionic mobility, with an order of magnitude larger temperature coefficient than for common sensor materials. The sensor included a platinum resistive heater and electrochemical impedance sensor encapsulated by thin film Parylene (FIG. 21). The sensor was affixed in a luer-lock fitting and external connections were achieved via Parylene ribbon cable. Flow of phosphate-buffered saline (PBS) was established and sensed by monitoring the passage of a thermal tracer (2 mA, 10 s current pulse) as a decrease in impedance. Flow rate was varied from 0 to 400 μL/min via peristaltic pump with minimum step sizes of 20 μL/min and impedance was measured at 10 kHz with a precision LCR meter. At this frequency, the response may be dominated by the solution resistance. Experiments were conducted at 21.0° C. (room temperature) and 37.0° C. (body temperature) in 1× PBS (a common analog for physiological fluids), with deionized water as a control. Flow was determined by converting impedance to a percentage of the baseline level and calculating the instantaneous rate of change when the thermal tracer was detected.

Figure 23:
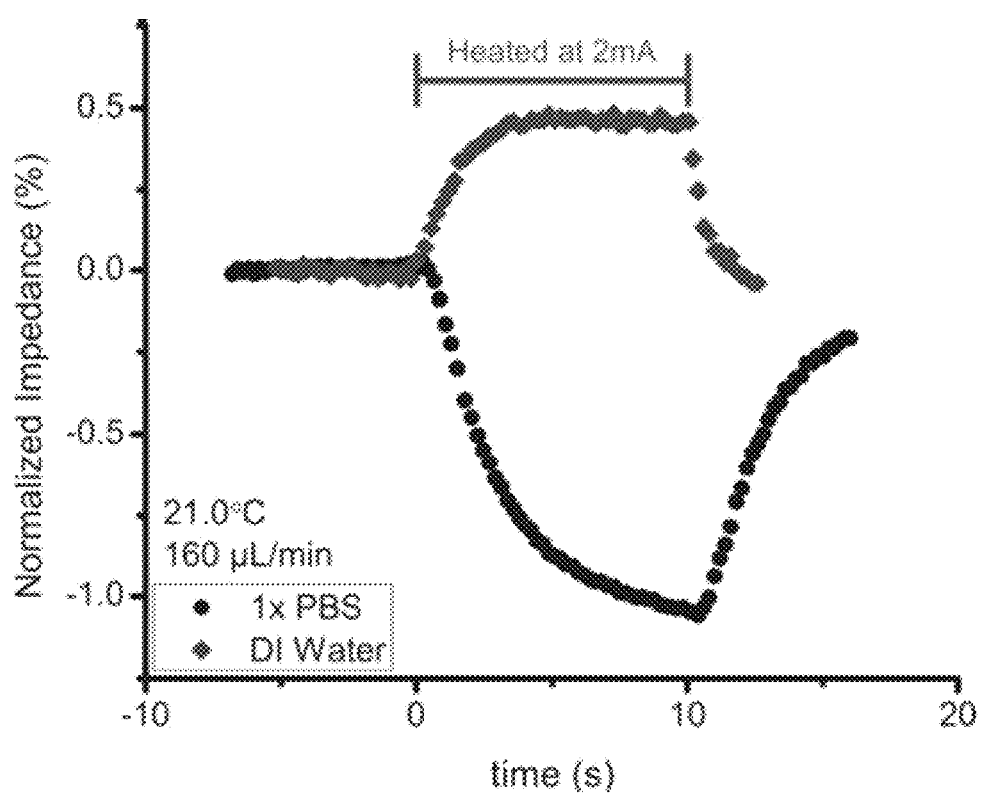
FIG. 23 illustrates an example of effects of heating on the electrochemical impedance of an electrode pair in 1× phosphate buffered saline (PBS) and deionized (DI) water.
Figure 24:
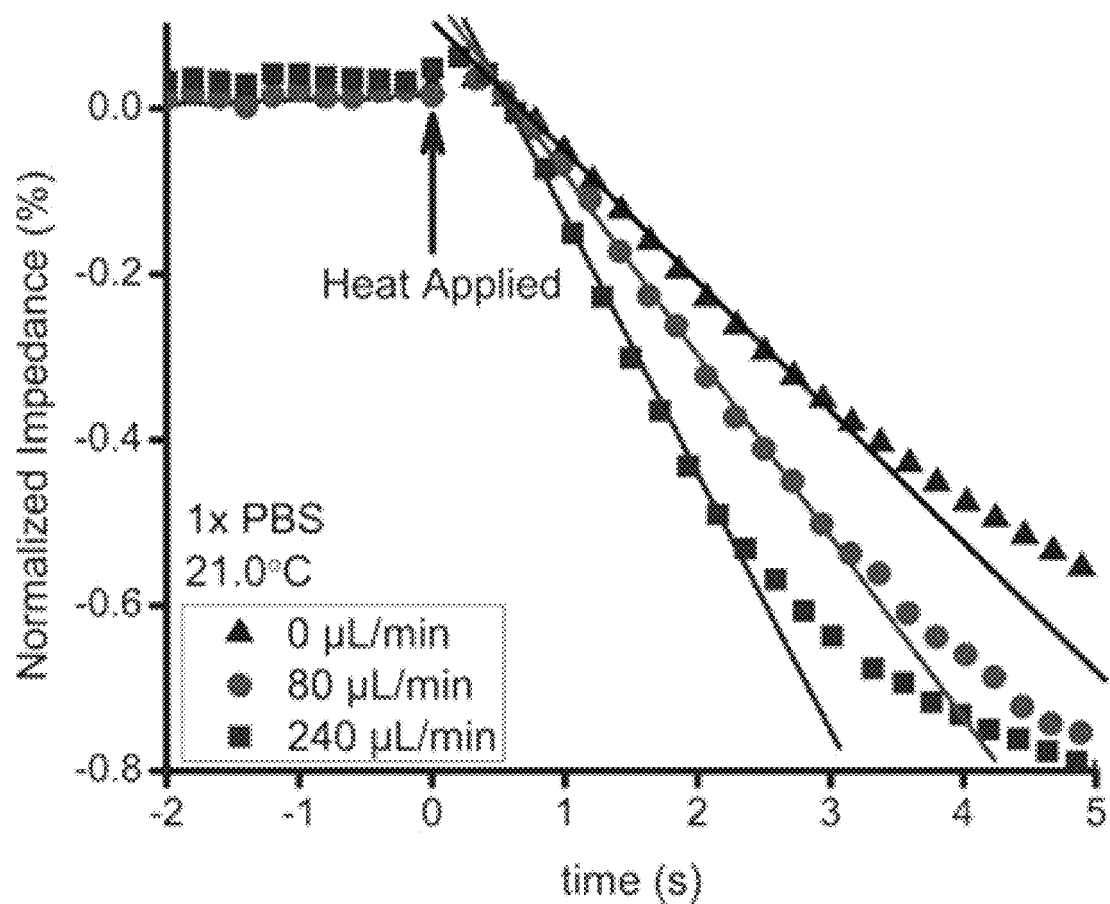
FIG. 24 illustrates an example of the rate of change of impedance upon heating being proportional to the flow velocity, and can be used to measure flow rate. This method may be useful for low flow rates where diffusion is the dominant force in heat transfer.
Figure 25:
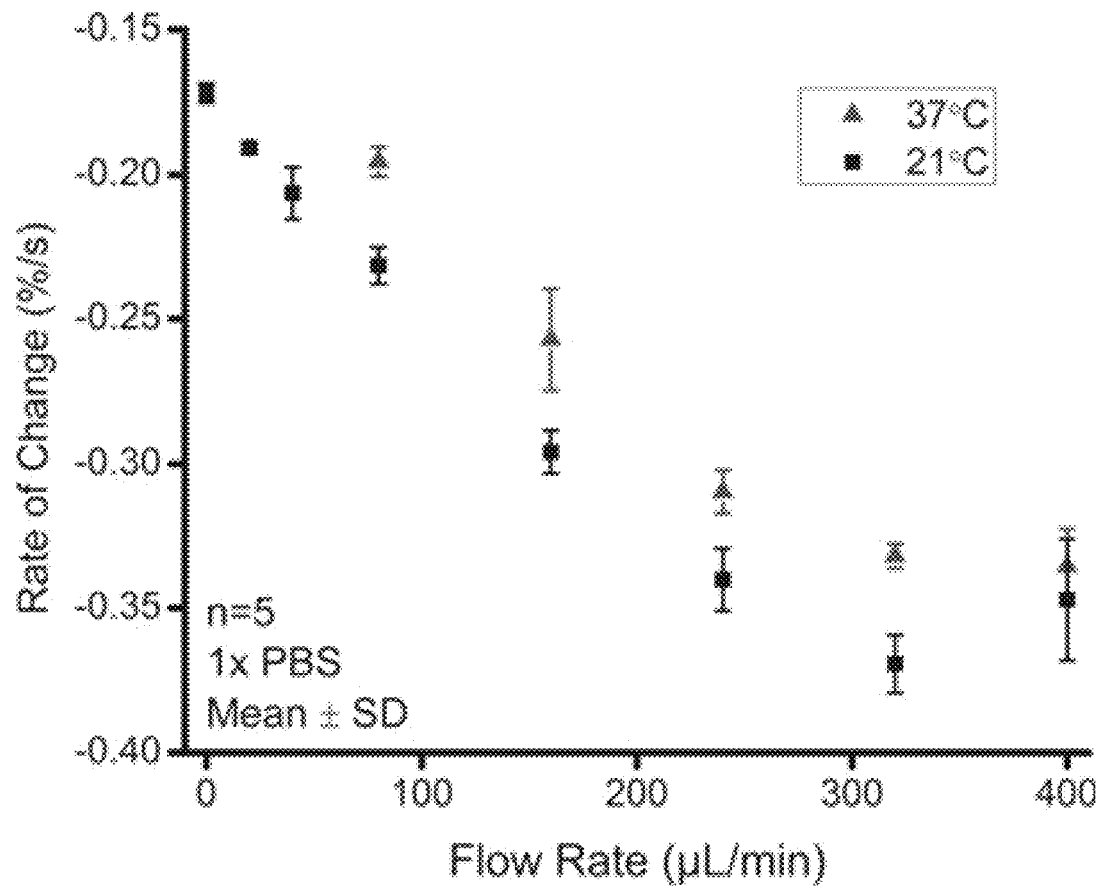
FIG. 25 illustrates an example of the rate of change of impedance being linearly related to flow rate for rates below 320 µL/min.

Impedance was seen to drop sharply when PBS is heated due to increased ionic mobility, but increases slightly for deionized water, possibly due to density change (FIG. 23). In PBS, the instantaneous rate of change in impedance may serve as an accurate measure of fluid flow (FIG. 24). The sensor clearly distinguishes flow differences of 20 μL/min over the majority of the tested flow range, with a LOD of 10.7 μl/min at no flow. The relationship between rate of change and flow is linear at low flow rates, but levels off at high rates, possibly due to tracer reaching the electrodes faster than detectable with our LCR meter (FIG. 25). Higher flow rates can be detected by increasing the distance between the heater and electrodes, or using multiple impedance sensors to increase the detectable flow range. At body temperature, the baseline rate of change increased, although the relationship between rate of change and flow remained constant. This may necessitate temperature calibration or assumption of steady ambient temperatures. One solution may be to utilize additional impedance-sensing electrodes separated by known distances to achieve more accurate time-of-flight measurements.

A micro time of flight (TOF) electrochemical impedance flow sensor (μEIFS) was developed for characterization of in vivo flow dynamics. The transducer utilizes EI measurement between electrode pairs to monitor the passage of an electrolytically generated gas bubble within flowing solution (10-1000 μL/min, <6% TOF variation). The μEIFS features biocompatible construction (only Parylene and Pt), low power consumption, and low profile thin film format which make it suited to chronic in vivo monitoring of flow with immediate application in monitoring of hydrocephalus.

Figure 26:
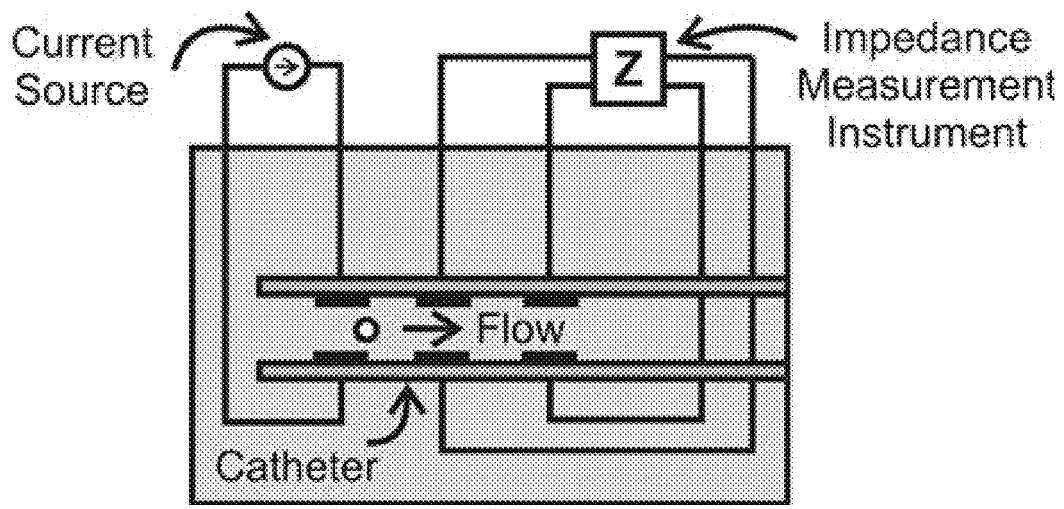
FIG. 26 illustrates an example of electrolysis being performed upstream of flow to generate a bubble that moves with the fluid flow. Two downstream electrode pairs may detect passage of bubble. Flow rate may be obtained through time-separated impedance spikes caused by detection of flow-induced movement of microbubble.
Figure 27:
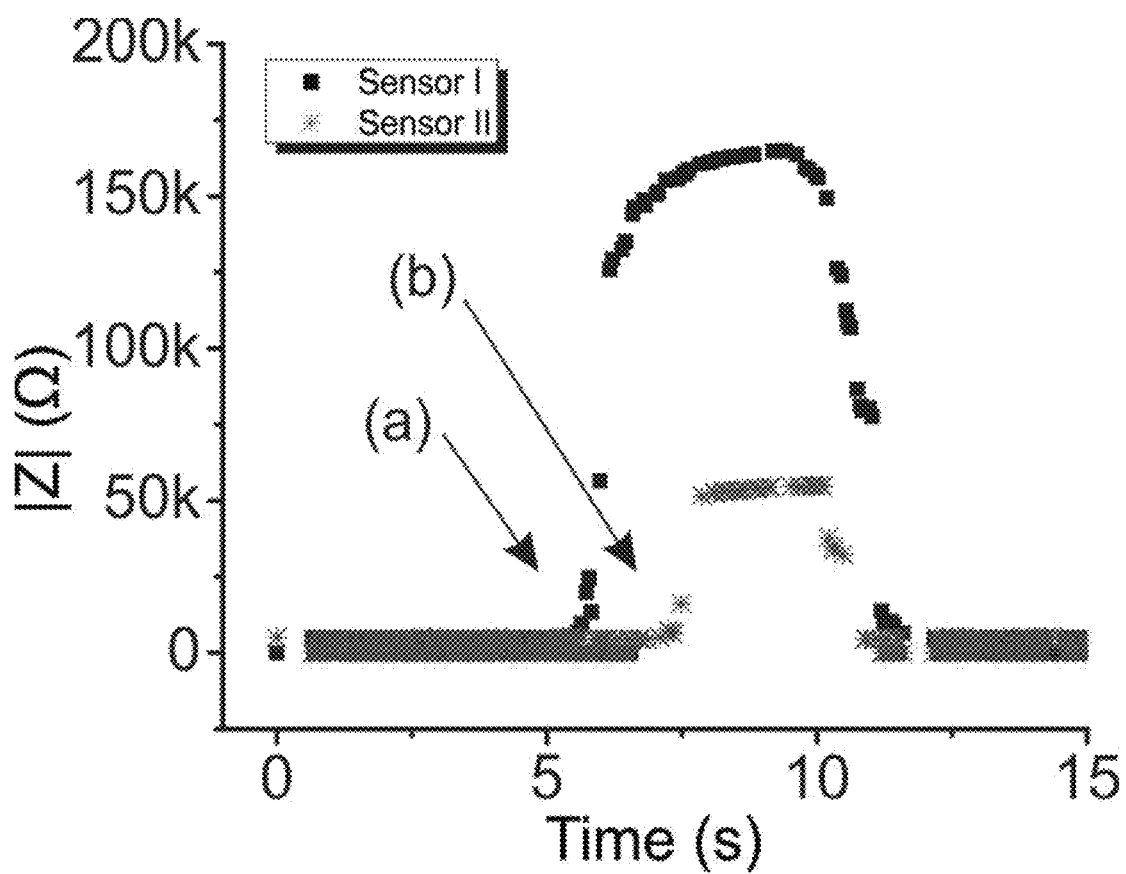
FIG. 27 illustrates an example of detection of a bubble at each electrochemical impedance sensor; time of flight may be derived from differences in rising edge time (a) and (b) of impedance response.

The μEIFS may include a Parylene thin film substrate with three pairs of Pt electrodes positioned in parallel to the direction of fluid flow. To improve temporal resolution, separate electrode pairs were dedicated for bubble electrolysis and measurement. First, a bubble may be electrolytically generated with the upstream pair of electrodes (FIG. 26). As the bubble travels downstream, it may disrupt the path of ionic current and manifests as increased electrochemical impedance at each downstream measurement electrode pair (FIG. 27). Given the predefined electrode geometry (FIG. 21), flow rate may be derived from the difference in the time of the onset of measured impedance change at these two electrode pairs, which corresponds to the passage of the leading edge of the bubble.

Devices were designed for integration within the lumen of a commercially available luer-lock interconnect (4 mm ID, FIG. 21). This configuration was selected to allow subsequent testing of sensors in line with an external ventricular drain (EVD) used in acute clinical settings for managing elevated intracranial pressure and draining cerebrospinal fluid (CSF). Devices were fabricated using well-established Parylene micromachining methods. To mimic biological fluids, phosphate buffer solution (1× PBS) was used for sensor characterization. Electrochemical impedance spectroscopy yielded 10 kHz as the optimum frequency (minimum system phase) for EI measurement. Multiplexed EI measurement (1 Vp-p, <1 nW) was conducted with a custom PCB attached to a LabVIEW interface to realize high temporal resolution (50 ms) for TOF measurement.

Figure 28:
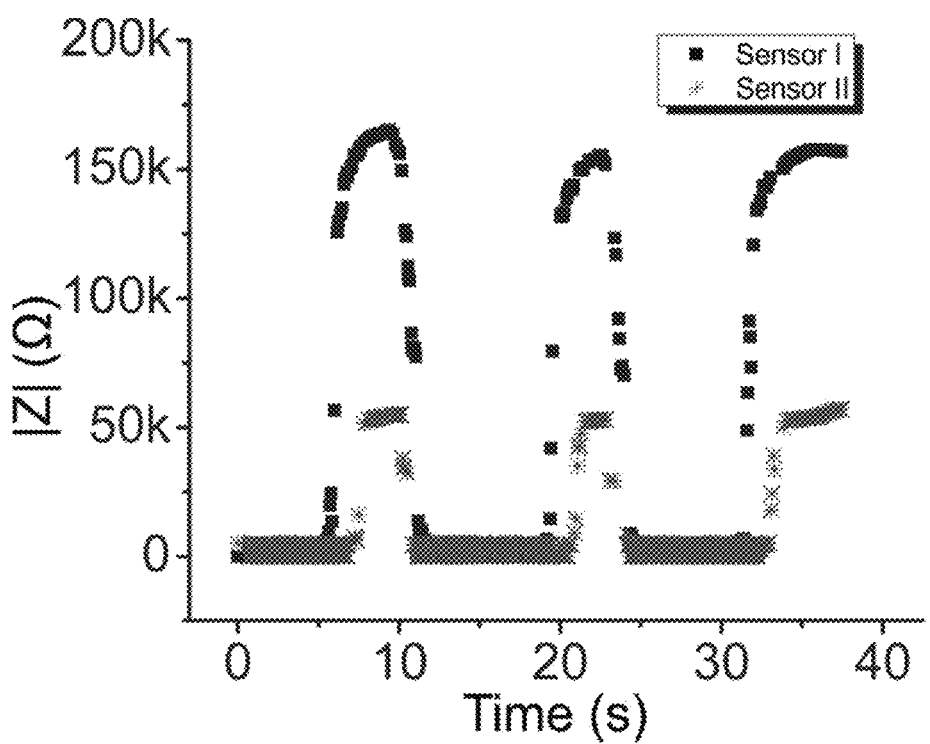
FIG. 28 illustrates an example of an impedance response of multiple bubbles passing through luer lock interconnect at 300 μL/min.
Figure 29:
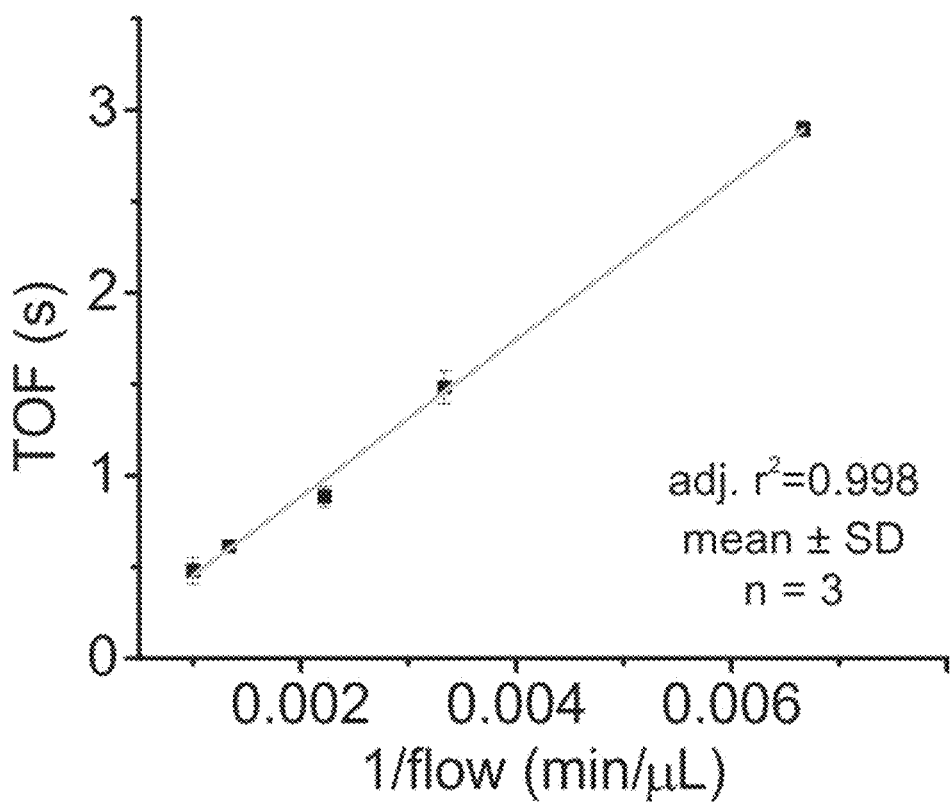
FIG. 29 illustrates an example of a relationship between flow rate and bubble time of flight that is inversely proportional. Trend also includes 10 μL/min (data not shown).

A bubble was electrolytically generated (50-70 μA, 30-45 s) within flowing PBS (10-1000 μL/min) at the upstream electrode pair and EI measurements were taken as it traversed downstream over the two sensing electrode pairs (FIG. 27 & FIG. 28). Spacing between EI sensing electrode pairs was investigated; 2500 μm was selected because TOF was indiscernible with electrode spacing of 500 μm. High precision measurement (limited by software rate of acquisition) of bubble TOF (SD <6% of mean) was achieved with the velocity range of 8.3-830×10-7 m/s. The volumetric flow rate was found to have an inversely proportional relationship (linearized, r2=0.99) with the time of flight (FIG. 29). Additional sensor characterization may be done by varying electrolyte composition, such as use of artificial and human CSF, sensor orientation and placement, electrode layout. Then sensors may be attached to EVDs in clinical settings to achieve in-human demonstration.

Following confirmation of each sensor separately, all three sensors were combined and fabricated on a Parylene C substrate (FIG. 2A1a). Bulk dimensions and respective orientation of the sensors were chosen to fit within the lumen of a luer-lock adaptor for use with external ventricular drain systems. A similar electrical packaging method using a ZIF connector was used to connect to the Parylene device. Two connector options for connection to the measurement system was explored: a standard input/output connector (Hirose) and a FFC. To package the devices into the luer-lock module, initially a small slit was milled into the top of the module and filed to remove resultant burrs from the milling process. The Parylene device of three sensors was threaded through the slit in the luer-lock module and either rested in the middle of the lumen, or was curled around the inner circumference of the lumen. Biocompatible epoxy was then used to fully encapsulate the milled slit and Parylene device to ensure no leakage points to the outside of the device.

Leakage tests were carried out on the fully packaged device and was found to sustain 100 mmHg for 1 hour (n=4). Additional tests may be performed to characterize sensor performance within the inline module, as well as the efficacy of the $H_2O_2$ plasma sterilization process on the inline modules. Efforts to shrink the module packaging to one that fits between an implanted valve and shunt may also be made.

Features

Features of what has been described may include:
1. Inclusion of one or more sensors on a flexible thin film substrate, such as Parylene
   - The use of Parylene micromachining to manufacture the sensors having small size and low profile directly on the flexible thin film substrate
   - The use of one or more such sensor modules distributed across a shunt
   - The direct integration of sensor modules onto a shunt or as discrete connectable units in line with a shunt
   - The use of sensors capable of measuring hydrodynamic parameters such as intracranial pressure (ICP), differential pressure across the shunt, shunt CSF flow, and catheter patency
      - The use of electrochemical impedance transduction to achieve pressure, flow, and patency measurements
      - The use of a biocompatible thin film polymer and metal as construction materials for the sensor and substrate
      - The use of platinum and Parylene C as the construction materials for such a sensing approach
      - The use of electroplated or conductive polymer deposition (PtIr, Nafion) to improve electrolysis efficiency or sensing techniques
   - The use of biological or chemical sensors to provide local measurements of relevant physiological biomarkers to inform treatment or adjust the shunt (e.g. non-invasively adjustable valve)
   - The use of environmental sensors such as pH or temperature to provide feedback data for optimal module and/or implant performance
   - The use of wireless data and power telemetry to allow remote, non-invasive monitoring of implanted sensors
2. The use of electrolytic bubbles as a tracer for time of flight flow sensing
   - Implementation of such a method using multiple pairs of electrodes spaced along and in the direction of the flow path
   - At least one pair of electrodes is used to electrolytically generate the bubble tracers
   - At least two pairs of electrodes with known separation distance are used to measure the time of bubble transit and therefore calculate the flow rate
   - The sensor can be fabricated using micromachining so as to allow miniature features suitable for application in small spaces, such as a catheter or shunt
   - The sensor can be fabricated on a flexible substrate to facilitate implementation in a flexible catheter or shunt
   - The sensor can be constructed of a biocompatible thin film polymer and metal
   - The polymer can be Parylene C
   - The metal can be platinum although other suitable metals may include titanium, iridium, and gold
   - The sensor may include guiding structures to direct the bubble tracers
   - The bubble tracers may be sized such that their center of mass aligns with the maximum flow velocity in the parabolic flow profile associated with a circular pipe
   - Multiple bubble tracers may be used in various positions to provide information about the flow profile.
3. The use of heated fluid as a means to modify the electrochemical impedance of flowing material
   - Implementation of such a method by using a heater and multiple pairs of electrodes spaced along and in the direction of the flow path
   - At least two pairs of electrodes with known separation distance are used to measure the transit time of a heat pulse and therefore calculate flow rate
   - At least one pair of electrodes is positioned upstream and one pair downstream of the heater to measure flow-induced difference in temperature upstream and downstream of the heater
   - The sensing system may be optimized to measure flow rate from the rate of heating at a single electrode pair upstream of the heater
   - The electrodes and heater may be constructed using micromachining so as to allow miniature features suitable for application in small spaces, such as a catheter or shunt
   - The sensing system can be fabricated on a flexible substrate to facilitate implementation in a flexible catheter or shunt
   - The sensing system can be constructed of a biocompatible thin film polymer and metal
   - The polymer can be Parylene C
   - The metal can be platinum although other suitable metals may include titanium, iridium, and gold
   - The heater may consist of a snaked platinum trace insulated with Parylene The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and/or advantages. These also include embodiments in which the components and/or steps are arranged and/or ordered differently.

For example, the individual structures need not be constructed on a single substrate and may be fabricated on separate substrates that are appropriately placed so as to achieve the desired function. Electrodes need not be microfabricated using thin film metals, but can instead be bulk metal electrodes, such as wire or discs. Implantable devices may have wired connectors or ports instead of wireless data transmission schemes.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

The scope of protection is limited solely by the claims that now follow. That scope is intended and should be interpreted to be as broad as is consistent with the ordinary meaning of the language that is used in the claims when interpreted in light of this specification and the prosecution history that follows, except where specific meanings have been set forth, and to encompass all structural and functional equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element proceeded by an "a" or an "an" does not, without further constraints, preclude the existence of additional elements of the identical type.

None of the claims are intended to embrace subject matter that fails to satisfy the requirement of Sections 101, 102, or 103 of the Patent Act, nor should they be interpreted in such a way. Any unintended coverage of such subject matter is hereby disclaimed. Except as just stated in this paragraph, nothing that has been stated or illustrated is intended or should be interpreted to cause a dedication of any component, step, feature, object, benefit, advantage, or equivalent to the public, regardless of whether it is or is not recited in the claims.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The invention claimed is:

1. A multi-sensor system comprising:
   a catheter that has a lumen, is flexible, is comprised of a polymer, and has a substantially circular cross section that has an outer diameter of no more than 0.5 cm; and
   two or more sensors that sense multiple characteristics of material flowing through the lumen in order to monitor the blockage or drainage status of said catheter, including at least two of the following: flow rate, pressure, and composition of the material.

2. The multi-sensor system of claim 1, wherein a portion of the two or more sensors is located on a flexible substrate that is separate from the catheter.

3. The multi-sensor system of claim 2, wherein the flexible substrate is Parylene C.

4. The multi-sensor system of claim 1, wherein the portion of at least one of the two or more sensors that is within the lumen does not materially block the material from flowing within the lumen.

5. The multi-sensor system of claim 1, wherein the portion of the two or more sensors that are within the lumen does not protrude within the lumen by more than 50 microns.

6. The multi-sensor system of claim 1, wherein the catheter has an interior wall that defines the lumen and wherein a portion of at least one of the two or more sensors is located on a portion of the interior wall.

7. The multi-sensor system of claim 1, further including a wireless communication system that wirelessly communicates information from the two or more sensors.

8. The multi-sensor system of claim 1, further comprising an inductor that wirelessly receives power that powers the two or more sensors.

9. The multi-sensor system of claim 1, further including a data processing system that performs computations on data generated by the two or more sensors.

10. The multi-sensor system of claim 1, wherein the two or more sensors includes a sensor that uses electrochemical transduction to determine a characteristic of the material flowing in the lumen.

* * * * *